(12) United States Patent
Yi et al.

(10) Patent No.: US 11,373,308 B2
(45) Date of Patent: Jun. 28, 2022

(54) X-RAY IMAGE PROCESSING METHOD AND X-RAY IMAGE PROCESSING APPARATUS

(71) Applicant: SAMSUNG ELECTRONICS CO., LTD., Suwon-si (KR)

(72) Inventors: Jaemock Yi, Suwon-si (KR); Mincheol Park, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 165 days.

(21) Appl. No.: 16/773,317

(22) Filed: Jan. 27, 2020

(65) Prior Publication Data
US 2020/0250824 A1    Aug. 6, 2020

(30) Foreign Application Priority Data

Feb. 1, 2019  (KR) .................. 10-2019-0013751

(51) Int. Cl.
- *A61B 6/00*    (2006.01)
- *G06T 7/00*    (2017.01)
- *G06T 7/593*   (2017.01)

(52) U.S. Cl.
CPC ............ *G06T 7/0014* (2013.01); *A61B 6/461* (2013.01); *A61B 6/505* (2013.01); *A61B 6/5247* (2013.01); *A61B 6/5282* (2013.01); *A61B 6/544* (2013.01); *A61B 6/583* (2013.01); *G06T 7/593* (2017.01); *G06T 2207/10028* (2013.01); *G06T 2207/10116* (2013.01); *G06T 2207/30008* (2013.01)

(58) Field of Classification Search
None
See application file for complete search history.

(56) References Cited

U.S. PATENT DOCUMENTS

| 6,683,934 | B1 | 1/2004 | Zhao et al. |
| 7,068,826 | B2* | 6/2006 | Jabri ................ A61B 6/405 |
| | | | 382/128 |
| 7,856,133 | B2 | 12/2010 | Nukui |
| 9,907,528 | B2 | 3/2018 | Yi et al. |
| 2003/0194120 | A1 | 10/2003 | Unger et al. |

(Continued)

FOREIGN PATENT DOCUMENTS

| EP | 3 351 176 A1 | 7/2018 |
| JP | 2012-143387 A | 8/2012 |

(Continued)

OTHER PUBLICATIONS

Communication dated Jun. 30, 2020, from the European Patent Office in European Application No. 20153662.0.

(Continued)

*Primary Examiner* — Hoon K Song
(74) *Attorney, Agent, or Firm* — Sughrue Mion, PLLC

(57) ABSTRACT

An X-ray image processing method, including obtaining a first X-ray image of an object including a plurality of materials including a first material and a second material different from the first material; obtaining three-dimensional (3D) information about the object using a 3D camera; obtaining first information about a thickness of the object based on the 3D information; and obtaining second information related to a stereoscopic structure of the first material by decomposing the first material from the object using the first information and the first X-ray image.

21 Claims, 20 Drawing Sheets

(56) References Cited

U.S. PATENT DOCUMENTS

| | | | |
|---|---|---|---|
| 2003/0215120 | A1 | 11/2003 | Uppaluri et al. |
| 2006/0008046 | A1 | 1/2006 | Ruhrnschopf |
| 2012/0170826 | A1 | 7/2012 | Jang et al. |
| 2013/0148776 | A1 | 6/2013 | Lee et al. |
| 2016/0213344 | A1 | 7/2016 | Yi et al. |
| 2018/0146942 | A1 | 5/2018 | Skalli |
| 2018/0206810 | A1 | 7/2018 | Song |
| 2021/0153833 | A1* | 5/2021 | Maack ................ A61B 6/5247 |

FOREIGN PATENT DOCUMENTS

| | | |
|---|---|---|
| JP | 5389965 B2 | 1/2014 |
| KR | 10-2009-0079867 A | 7/2009 |
| KR | 10-2016-0129302 A | 11/2016 |

OTHER PUBLICATIONS

Communication dated Jun. 9, 2020, from the European Patent Office in European Application No. 20153699.2.

\* cited by examiner

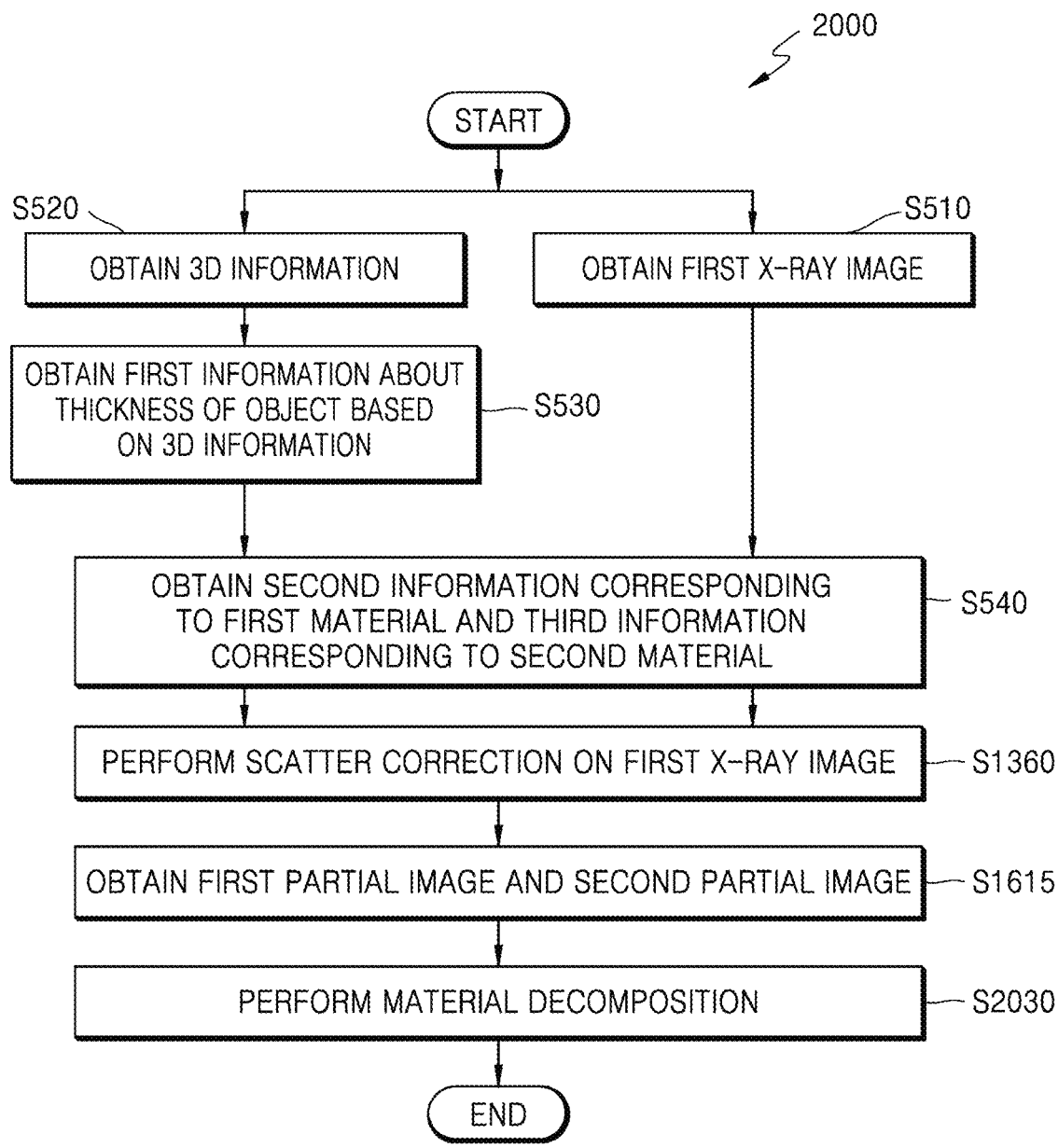

X-RAY IMAGE PROCESSING METHOD AND X-RAY IMAGE PROCESSING APPARATUS

CROSS-REFERENCE TO RELATED APPLICATION

This application is based on and claims priority under 35 U.S.C. § 119 to Korean Patent Application No. 10-2019-0013751, filed on Feb. 1, 2019, in the Korean Intellectual Property Office, the disclosure of which is incorporated by reference herein in its entirety.

BACKGROUND

1. Field

The disclosure relates to an X-ray image processing method for obtaining information related to an object by analyzing an X-ray image and an X-ray image processing apparatus using the X-ray image processing method.

2. Description of Related Art

An X-ray apparatus may be a medical imaging apparatus that obtains images of internal structures of a human body by transmitting an X-ray through the human body. The X-ray apparatus may obtain medical images of an object more simply within a shorter time than other medical imaging apparatuses including a magnetic resonance imaging (MRI) apparatus and a computed tomography (CT) apparatus. Therefore, the X-ray apparatus is widely used in simple chest imaging, simple abdomen imaging, simple skeleton imaging, simple nasal sinus imaging, simple neck soft tissue imaging, and breast imaging.

X-rays are electromagnetic waves having wavelengths ranging from 0.01 Å to 100 Å, and may be transmitted through an object and thus are widely used in medical devices for imaging the inside of a living body or are used in non-destructive testing devices in the industry.

An X-ray apparatus using X-rays may obtain an X-ray image of an object by transmitting X-rays emitted from an X-ray source through the object and detecting an intensity difference between the transmitted X-rays by using an X-ray detector. Accordingly, an internal structure of the object may be detected and the object may be diagnosed by using the X-ray image. The X-ray apparatus easily detects the internal structure of the object by using the fact that transmittances of the X-rays vary according to a density of the object and atomic numbers of atoms within the object. In general, an X-ray apparatus may generate a projection image corresponding to an object by two-dimensionally imaging the object. Accordingly, one X-ray image obtained through one X-ray imaging operation may not be suitable for measuring a stereoscopic structure of the object, a measurement value (for example a thickness of an organ or tissue in the object) corresponding to the stereoscopic structure of the object, or characteristic values (for example a volume of fat in the object) of a plurality of different materials of the object.

Recently, apparatuses and methods have been developed for obtaining a stereoscopic structure of an object, a measurement value (for example a thickness of an organ or tissue in the object) corresponding to the stereoscopic structure of the object, or characteristics values (for example a volume of fat in the object) of a plurality of different materials of the object, by using a plurality of X-ray images obtained through multiple X-ray imaging operations that emit X-rays having a plurality of energy bands to the object.

However, because X-rays emitted to an object for X-ray imaging are radioactive, the X-rays are harmful to humans. Accordingly, a user may desire to perform X-ray imaging while minimizing a radiation dose exposed to a patient including the object to be imaged. Accordingly, when X-ray imaging is performed multiple times as described above, a radiation dose exposed to the patient is increased. Also, when X-ray imaging is performed multiple times as described above, image quality is reduced due to movements of the patient or an internal organ.

Also, an accurate diagnosis may be made only when information about materials of an object is more accurately measured from an X-ray image. Hence, it is desirable to rapidly and accurately measure the information about the materials of the object from the X-ray image.

Accordingly, there is a demand for a method and apparatus for accurately obtaining various information about an object while minimizing a radiation dose exposed to a patient or the number of times X-ray imaging is performed.

SUMMARY

Provided are an X-ray image processing method of obtaining information about two or more different materials included in an object by using one X-ray image and an X-ray image processing apparatus using the X-ray image processing method.

Particularly provided are an X-ray image processing method of obtaining information about soft tissue and bones by using a first X-ray image obtained by emitting an X-ray having a single energy band to an object and an X-ray image processing apparatus using the X-ray image processing method.

Additional aspects will be set forth in part in the description which follows and, in part, will be apparent from the description, or may be learned by practice of the presented embodiments.

In accordance with an aspect of the disclosure, an X-ray image processing method includes obtaining a first X-ray image of an object including a plurality of materials including a first material and a second material different from the first material; obtaining three-dimensional (3D) information about the object using a 3D camera; obtaining first information about a thickness of the object based on the 3D information; and obtaining second information related to a stereoscopic structure of the first material by decomposing the first material from the object using the first information and the first X-ray image.

The X-ray image processing method may further include obtaining third information related to a stereoscopic structure of the second material, based on the first information and the second information.

The second information may be obtained based on the first information and X-ray absorption characteristics shown in the first X-ray image.

The first material may be soft tissue, and the second material may be a bone.

The second information may include at least one of a thickness of the soft tissue, a volume of the soft tissue, a volume ratio of the soft tissue, and an areal density of the soft tissue, and the third information may include at least one of a thickness of the bone, a volume of the bone, a volume ratio of the bone, and an areal density of the bone.

The second information may include information about a thickness of the first material, and the third information may include information about a thickness of the second material.

The X-ray image processing method may further include performing scatter correction on the first X-ray image, based on the second information and the third information.

The X-ray image processing method may further include measuring a distance from the 3D camera to a surface of the object, based on the 3D information, wherein the first information about the thickness of the object is obtained based on the distance to the surface of the object.

The X-ray image processing method may further include obtaining a scatter-corrected first X-ray image, by performing scatter correction on the first X-ray image based on the second information and the third information; and updating the second information and the third information based on the scatter-corrected first X-ray image.

The X-ray image processing method may further include generating, based on the second information and the third information, a scatter map showing a distribution of a scattered X-ray in the first X-ray image; and the scatter-corrected first X-ray image may be obtained by using the scatter map to remove a noise signal corresponding to the scattered X-ray from the first X-ray image.

The X-ray image processing method may further include obtaining, based on the second information and the third information, a first virtual X-ray image by performing projection simulation on the object; and determining whether to update the second information, the third information, and the scatter map based on a result of a comparison between the first virtual X-ray image and the first X-ray image.

The X-ray image processing method may further include generating, through the projection simulation, a projection image by transmitting an incident X-ray through a phantom corresponding to the object; and generating, based on the second information and the third information, the scatter map showing a distribution of a scattered X-ray in the first X-ray image; and the first virtual X-ray image may be obtained by adding the projection image and the scatter map.

The X-ray image processing method may further include outputting a user interface screen including at least one of the first information, the second information, or the third information.

The first X-ray image may be obtained by emitting an X-ray having a single energy band to the object.

In accordance with an aspect of the disclosure, an X-ray image processing apparatus includes a data interface configured to obtain a first X-ray image of an object including a plurality of materials including a first material and a second material different from the first material; and obtain three-dimensional (3D) information about the object using a 3D camera; and an image processor including at least one processor configured to execute at least one instruction to obtain first information about a thickness of the object based on the 3D information, and obtain second information related to a stereoscopic structure of the first material by decomposing the first material from the object using the first information and the first X-ray image.

The image processor may be further configured to execute the at least one instruction to obtain third information related to a stereoscopic structure of the second material based on the first information and the second information.

The first material may be soft tissue, and the second material may be a bone.

The image processor may be further configured to execute the at least one instruction to perform scatter correction on the first X-ray image based on the second information and the third information.

The image processor may be further configured to execute the at least one instruction to measure a distance from the 3D camera to a surface of the object based on the 3D information and to obtain the first information about the thickness of the object based on the distance to the surface of the object.

In accordance with an aspect of the disclosure, a non-transitory computer-readable medium stores instructions which, when executed by at least one processor, cause the processor to execute an X-ray image processing method on a computer, the X-ray image processing method including: obtaining a first X-ray image of an object including a plurality of materials including a first material and a second material different from the first material; obtaining three-dimensional (3D) information about the object by using a 3D camera; obtaining first information about a thickness of the object based on the 3D information; and obtaining second information related to a stereoscopic structure of the first material by decomposing the first material from the object using the first information and the first X-ray image.

In accordance with an aspect of the disclosure, X-ray image processing method includes obtaining a first X-ray image of an object including soft tissue and bone; determining X-ray absorption characteristics of the object based on the first X-ray image; obtaining three-dimensional (3D) information about the object using a 3D camera; determining a thickness of the object based on the 3D information; determining a thickness of the bone included in the object based on the determined thickness of the object and the determined X-ray absorption characteristics; and determining a thickness of the soft tissue included in the object by subtracting the determined thickness of the bone from the determined thickness of the object.

The X-ray image processing method may further include determining a volume of the soft tissue and a volume of the bone based on the determined thickness of the soft tissue and the determined thickness of the bone.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 20 is a flowchart illustrating an X-ray image processing method according to another embodiment.

DETAILED DESCRIPTION

Figure 1:
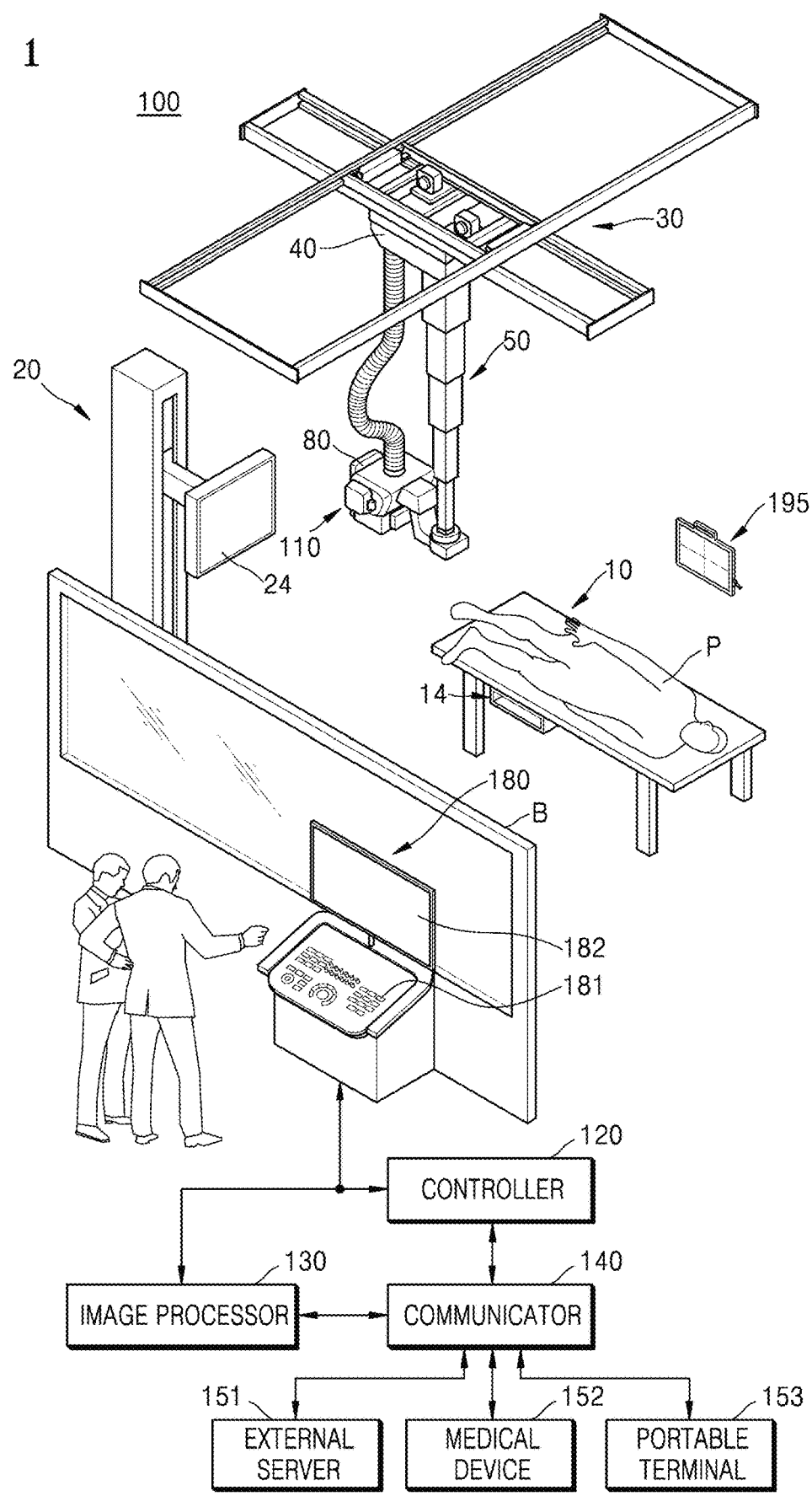
FIG. 1 is a view illustrating a configuration of an X-ray apparatus according to an embodiment.

Hereinafter, principles and embodiments of the disclosure will be described in detail in order to fully convey the scope and enable one of ordinary skill in the art to embody and practice the disclosure. The embodiments may be implemented in various forms.

The same reference numerals denote the same elements throughout the specification. All elements of embodiments are not described in the specification, and descriptions of matters well known in the art to which the disclosure pertains or repeated descriptions between embodiments will be omitted. Terms such as "part" and "portion" used herein denote those that may be embodied by software or hardware, and according to embodiments, a plurality of parts or portions may be embodied by a single unit or element, or a single part or portion may include a plurality of elements. Operation principles and embodiments will now be explained with reference to the accompanying drawings.

Throughout the disclosure, the expression "at least one of a, b or c" indicates only a, only b, only c, both a and b, both a and c, both b and c, all of a, b, and c, or variations thereof.

An image used herein may include any medical image acquired by various medical imaging apparatuses such as a magnetic resonance imaging (MRI) apparatus, a computed tomography (CT) apparatus, an ultrasound imaging apparatus, or an X-ray apparatus.

Also, in the present specification, an "object," which is a thing to be imaged, may include a human, an animal, or a part thereof. For example, an object may include a body part (for example an organ) or a phantom.

FIG. 1 is a view illustrating a configuration of an X-ray apparatus according to an embodiment. FIG. 1 will be described as relating to an embodiment in which the X-ray apparatus is a fixed X-ray apparatus.

Referring to FIG. 1, an X-ray apparatus 100 includes an X-ray emitter 110 that generates and emits an X-ray, an X-ray detector 195 that detects the X-ray emitted from the X-ray emitter 110 and transmitted through an object, and a workstation 180 that receives a command from a user and provides information. Also, the X-ray apparatus 100 may include a controller 120 that controls the X-ray apparatus 100 according to the input command and a communicator 140 that communicates with an external device.

Some or all of elements of the controller 120 and the communicator 140 may be included in the workstation 180 or may be provided separately from the workstation 180.

The X-ray emitter 110 may include an X-ray source that generates an X-ray and a collimator that adjusts an emission region of the X-ray generated by the X-ray source.

A guide rail 30 may be provided on the ceiling of an examination room in which the X-ray apparatus 100 is located, the X-ray emitter 110 may be connected to a movable carriage 40 that moves along the guide rail 30 to move the X-ray emitter 110 to a position corresponding to an object P, and the movable carriage 40 and the X-ray emitter 110 may be connected through a foldable post frame 50 to adjust a height of the X-ray emitter 110.

An input interface 181 that receives a command of the user and a display 182 that displays information may be provided in the workstation 180.

The input interface 181 may receive a command for an imaging protocol, imaging conditions, imaging timing, and position control of the X-ray emitter 110. Examples of the input interface 181 may include a keyboard, a mouse, a touchscreen, a voice recognizer, and any other type of interface.

The display 182 may display a screen for guiding the user's input, an X-ray image, a screen showing a state of the X-ray apparatus 100, and any other information.

The controller 120 may control imaging timing, imaging conditions, and any other aspect of the X-ray emitter 110 according to a command input from the user, and may generate a medical image by using image data received from the X-ray detector 195. Also, the controller 120 may control a position or a posture of a mounting portion 14 or 24 on which the X-ray emitter 110 or the X-ray detector 195 is mounted according to a position of the object P and an imaging protocol.

In an embodiment, the X-ray apparatus 100 may further include an image processor 130. The image processor 130 may generate a medical image by using image data received from the X-ray detector 195, and may include a memory in which a program for performing an image generating operation is stored and a processor for executing the stored program.

Also, in an embodiment, the controller 120 may include the image processor 130. That is, the image processor 130 may be at least one of at least one processor included in the controller 120.

As described above, an operation of generating a medical image may be performed by at least one of the controller 120 or the image processor 130. FIG. 1 will be described as relating to an embodiment in which an operation of generating a medical image is performed by the controller 120.

The controller 120 may include a memory in which a program for performing the above operations and following operations is stored and a processor for executing the stored program. The controller 120 may include a single processor or may include a plurality of processors, and in the latter case, the plurality of processors may be integrated on one chip or may be physically separated.

The X-ray apparatus 100 may be connected to an external device 150 (for example an external server 151, a medical device 152, or a portable terminal 153 (for example a smartphone, a tablet PC, or a wearable device)) through the communicator 140 and may transmit or receive data to or from the external device 150.

The communicator 140 may include one or more elements that enable communication with the external device 150, and may include at least one of, for example, a short-range communication module, a wired communication module, or a wireless communication module.

Also, the communicator 140 may receive a control signal from the external device 150 and may transmit the received control signal to the controller 120 so that the controller 120 controls the X-ray apparatus 100 according to the received control signal.

Also, the controller 120 may control the external device 150 according to a control signal of the controller 120 by transmitting the control signal to the external device 150 through the communicator 140. For example, the external device 150 may process data of the external device 150 according to the control signal of the controller 120 received through the communicator 140.

Also, the communicator 140 may further include an internal communication module that enables communication among elements of the X-ray apparatus 100. A program for controlling the X-ray apparatus 100 may be installed in the external device 150, and may include instructions for performing some or all of operations of the controller 120.

The program may be previously installed in the portable terminal 153, or a user of the portable terminal 153 may download the program from a server that provides an application and may install the program. A recording medium in which the program is stored may be included in the server that provides the application.

The X-ray detector 195 may be implemented as a fixed X-ray detector fixed to a stand 20 or a table 10, may be detachably mounted on the mounting portion 14 or 24, or may be implemented as a portable X-ray detector that may be used at any position. The portable X-ray detector may be implemented as a wired detector or a wireless detector according to a data transmission method and a power supply method.

The X-ray detector 195 may be included or may not be included in the X-ray apparatus 100. In the latter case, the X-ray detector 195 may be registered in the X-ray apparatus 100 by the user. Also, in both cases, the X-ray detector 195 may be connected to the controller 120 through the communicator 140 and may receive a control signal or may transmit image data.

A sub-user interface 80 that provides information to the user and receives a command from the user may be provided on a side surface of the X-ray emitter 110 and may perform some or all of functions of the input interface 181 and the display 182 of the workstation 180.

When all or some of elements of the controller 120 and the communicator 140 are provided separately from the workstation 180, the elements may be included in the sub-user interface 80 provided on the X-ray emitter 110.

Although the X-ray apparatus 100 is a fixed X-ray apparatus connected to the ceiling of the examination room in FIG. 1, the X-ray apparatus 100 may include an X-ray apparatus having any of various structures known to one of ordinary skill in the art such as a C-arm X-ray apparatus or a mobile X-ray apparatus.

An X-ray image (for example, a first X-ray image) according to an embodiment may be obtained by the X-ray apparatus 100 of FIG. 1. In detail, the X-ray apparatus 100 may obtain an X-ray image of an object through X-ray imaging or raw data used to obtain the X-ray image. For example, when the X-ray detector 195 detects an X-ray transmitted through the object, the raw data may be a signal obtained by electrically converting the number of X-ray photons detected by the X-ray detector 195.

In order to easily read an X-ray image or easily make a diagnosis by using the X-ray image, an X-ray image processing apparatus may analyze the X-ray image obtained through X-ray imaging and may use an analysis result. The X-ray image that is obtained by emitting an X-ray to an object of a patient and detecting the X-ray passing through the object may be a medical image showing the inside of the object. Also, the X-ray image may refer to not only an image visually representing the object but also data obtained to generate the image.

Hereinafter, a medical image obtained by directly emitting an X-ray to the object of the patient and performing X-ray imaging by using the X-ray apparatus 100 is referred to as an 'X-ray image', and an X-ray image obtained without directly emitting an X-ray to the object of the patient through X-ray imaging is referred to as a 'virtual X-ray image'.

In an embodiment, the X-ray image processing apparatus may refer to an electronic device that i) may obtain predetermined information by using an X-ray image, ii) may obtain diagnostic information by analyzing the X-ray image, or iii) may process, generate, correct, update, or display all images or information used for diagnosis based on the X-ray image.

In detail, the X-ray image processing apparatus according to an embodiment may be an electronic device that decomposes a plurality of different materials (for example bones and soft tissue) and obtains information about each of the plurality of different materials based on an X-ray image.

Also, the X-ray image processing apparatus according to an embodiment may analyze an X-ray image obtained by the X-ray apparatus 100 by using a computer and may generate and/or use an analysis result by using image processing technology such as a neural network system that performs a computation by using an artificial intelligence (AI) technology, machine learning, or a computer-aided detection (CAD) system.

Hereinafter, an X-ray image processing method according to an embodiment which may obtain information about each of a plurality of materials included in an object from an X-ray image and three-dimensional (3D) information obtained by using a 3D camera and an X-ray image processing apparatus using the X-ray image processing method will be described with reference to the attached drawings.

The X-ray image processing apparatus according to an embodiment may exist in various forms. For example, the X-ray image processing apparatus according to an embodiment may be formed in a console or the workstation 180 of the X-ray apparatus 100 of FIG. 1.

As another example, the X-ray image processing apparatus according to an embodiment may be formed in a device or server separate from the X-ray apparatus 100. The device or server separate from the X-ray apparatus 100 may be referred to as an 'external device'. Examples of the external device may include the server 151, the medical device 152, and the portable terminal 153 of FIG. 1, and the external device may receive an actual X-ray image through a wired/wireless communication network with the X-ray apparatus 100. For example, the X-ray image processing apparatus according to an embodiment may be formed in an analysis workstation, an external medical device, a picture archiving communication system (PACS) server, a PACS viewer, an external medical server, or a hospitable server.

Figure 2:
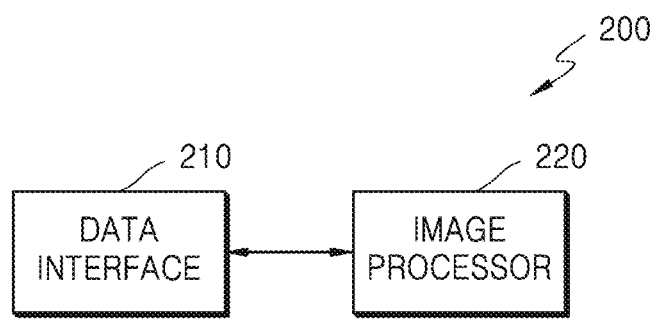
FIG. 2 is a block diagram illustrating an X-ray image processing apparatus according to an embodiment.

FIG. 2 is a block diagram illustrating an X-ray image processing apparatus according to an embodiment.

Referring to FIG. 2, an X-ray image processing apparatus 200 according to an embodiment may include a data interface 210 and an image processor 220.

Also, when the X-ray image processing apparatus 200 is included in the X-ray apparatus 100 of FIG. 1, the image processor 220 of FIG. 2 may correspond to the controller 120 or the image processor 130 of FIG. 1.

An X-ray image may be an image obtained by projecting an X-ray to an object and imaging the inside of the object. Accordingly, the inside of the object is imaged in a superimposed manner in an X-ray emission direction. In detail, a plurality of materials included in the object in the X-ray image may be imaged in an overlapping manner. Accordingly, it may be difficult to obtain information related to a stereoscopic structure of the inside of the object or a stereoscopic structure of each of the materials included in the object by using one X-ray image.

In an embodiment, information related to a stereoscopic structure of a first material may be obtained by decomposing the first material from the object, by using 3D information obtained by using a 3D camera and one X-ray image (for example, a first X-ray image).

The data interface 210 obtains the first X-ray image generated by imaging the object formed of a plurality of materials including the first material and a second material and the 3D information of the object obtained by using the 3D camera. The first material and the second material included in the object are different materials. In an embodiment, the data interface 210 may obtain raw data for generating the first X-ray image. For example, the data interface 210 may form the raw data for generating the first X-ray image as an electrical signal indicating an X-ray detection result.

In detail, the object may be formed of a plurality of different materials. In detail, the object may be formed of body forming materials such as soft tissue, bones, and blood. Also, examples of the soft tissue may include muscles, fat, cartilage, fibrous tissue, and blood vessels.

In detail, the first material and the second material may be materials having different X-ray attenuation characteristics from among the materials included in the object. That is, the first material and the second material may have different X-ray attenuation coefficients.

The first X-ray image may be an X-ray image obtained by emitting an X-ray having a single energy band to the object. That is, the first X-ray image is one X-ray image corresponding to the single energy band.

In detail, the object may include a body part including at least one of cells, tissue, organs, or other body forming materials. In detail, the object may include a patient's arm, leg, abdomen, and/or breast. For example, materials included in the arm may be roughly divided into an arm bone and soft tissue surrounding the arm bone. For example, the first X-ray image may be an X-ray image obtained by emitting an X-ray having a single energy band to a body part of the patient formed of a bone and soft tissue such as an arm and performing imaging by using the X-ray transmitted and detected through the arm of the patient.

The 3D information may be information obtained by imaging the object by using the 3D camera, and may include information about a stereoscopic structure of the object. In detail, the 3D information may include depth information about the object. In detail, a depth may correspond to a distance value indicating how far the object is separated from the 3D camera. That is, the 3D information may include depth information that is information about a distance from the 3D camera to a surface of the object.

The 3D camera refers to an apparatus for capturing an image of a subject to provide a sense of depth to the object imaged in an image. In detail, the 3D camera may include a stereo camera or a depth camera, and may obtain the 3D information about the subject (for example the patient) in a scene. For example, an example operation of obtaining the 3D information by using the stereo camera will be described in detail with reference to FIGS. 8 and 9.

The image processor 220 may perform an operation such as generation of an image, processing of the image, conversion of the image, and/or analysis of the image. The processing of the image may include an operation of obtaining target information from the image by analyzing the image.

The image processor 220 includes at least one processor that executes at least one instruction. The image processor 220 controls the following operations to be performed by executing the at least one instruction. In detail, the image processor 220 obtains first information about a thickness of the object based on the 3D information by executing the at least one instruction. The image processor 220 obtains second information related to a stereoscopic structure of the first material by decomposing the first material from the object, based on the first information and the first X-ray image. In detail, the information related to the stereoscopic structure may include information about a thickness, a volume, a shape, a geometric structure, and any other information. In detail, the second information may be information indicating a thickness of the first material included in the object in an X-ray emission direction.

Also, the image processor 220 may obtain third information related to a stereoscopic structure of the second material, based on the first information and the second information.

In an embodiment, the first material may be soft tissue or a bone. The second material may be a bone or soft tissue.

The following description relates to an embodiment in which the first material is soft tissue and the second material is a bone.

That is, according to an embodiment, the second information related to the stereoscopic structure of the first material is obtained by decomposing the first material from the object, by using 3D information and one X-ray image (for example, the first X-ray image).

In detail, information related to a stereoscopic structure may be information necessary to three-dimensionally represent an object or at least one material of the object, instead of information that may be recognized from a two-dimensional (2D) image showing the object or the at least one material of the object.

In detail, the second information may include information about at least one material included in the object, for example, a thickness, a volume, a volume ratio, an areal density, a shape, a geometric structure, and any other information of the first material. Also, the third information may include information about at least one material included in the object, for example, a thickness, a volume, a volume ratio, an areal density, a shape, a geometric structure, and any other information of the second material. Also, the term "thickness" may refer to a transmission thickness or a projection thickness that may be a length of a path through which an X-ray passes through the object.

In an embodiment, a process of obtaining the second information about the first material by decomposing the first material from the object may be referred to as "material decomposition".

Also, the data interface 210 may obtain the 3D information and the first X-ray image by using various methods.

For example, when the X-ray image processing apparatus 200 is formed inside a medical imaging apparatus (for example the X-ray apparatus 100), the X-ray image processing apparatus 200 itself may obtain the first X-ray image by performing X-ray imaging. As another example, when the X-ray image processing apparatus 200 is provided separately from the medical imaging apparatus (for example the X-ray apparatus 100), the X-ray image processing apparatus 200 may receive the first X-ray image through a wired/wireless communication network from the medical imaging apparatus. In this case, the data interface 210 may include thereinside a communicator (for example a communicator 415 of FIG. 4), and may receive the first X-ray image through the communicator provided inside the data interface 210.

An example of an operation and a configuration in which the data interface 210 itself obtains an X-ray image by performing X-ray imaging will be described in detail with reference to FIG. 3.

Also, the data interface 210 may include the 3D camera. The data interface 210 may obtain the 3D information through the 3D camera. In detail, the data interface 210 may obtain the 3D information by performing 3D imaging on the object by using the 3D camera.

Also, the data interface 210 may receive the 3D information through a wired/wireless communication network. In this case, the data interface 210 may include thereinside a communicator (for example the communicator 415 of FIG. 4), and may receive the 3D information through the communicator provided inside the data interface 210. An example of an operation and a configuration in which the data interface 210 itself obtains the 3D information by performing 3D imaging will be described in detail with reference to FIGS. 3, 8, and 9.

Also, the image processor 220 includes at least one processor that executes one or more instructions. Each of the at least one processor may perform a predetermined operation by executing at least one of the one or more instructions.

Also, the image processor 220 may include an internal memory and at least one processor that executes at least one stored program. In detail, the internal memory of the image processor 220 may store one or more instructions. The at least one processor included in the image processor 220 may perform a predetermined operation by executing at least one of one or more instructions stored in the internal memory of the image processor 220.

In detail, the image processor 220 may include a random-access memory (RAM) for storing signals or data input from the outside of the X-ray image processing apparatus 200 or used as a storage corresponding to various tasks performed by the X-ray image processing apparatus 200, a read-only memory (ROM) for storing a plurality of instructions and/or a control program for controlling the X-ray image processing apparatus 200, and at least one processor. The processor may include a graphics processing unit (GPU) for performing graphics processing on a video. The processor may be implemented as a system-on-chip (SoC) in which a core is combined with a GPU. The processor may include a single-core, a dual-core, a triple-core, a quad-core, and a multiple core thereof.

Also, the at least one processor included in the image processor 220 may control operations performed by the X-ray image processing apparatus 200, and may control other elements included in the X-ray image processing apparatus 200 to perform a predetermined operation. Accordingly, although the image processor 220 is described as controlling predetermined operations to be performed, it will be understood that the at least one processor included in the image processor 220 controls the predetermined operations to be performed.

Example of elements of the X-ray image processing apparatus 200 will be described with reference to FIGS. 3 and 4.

Figure 3:
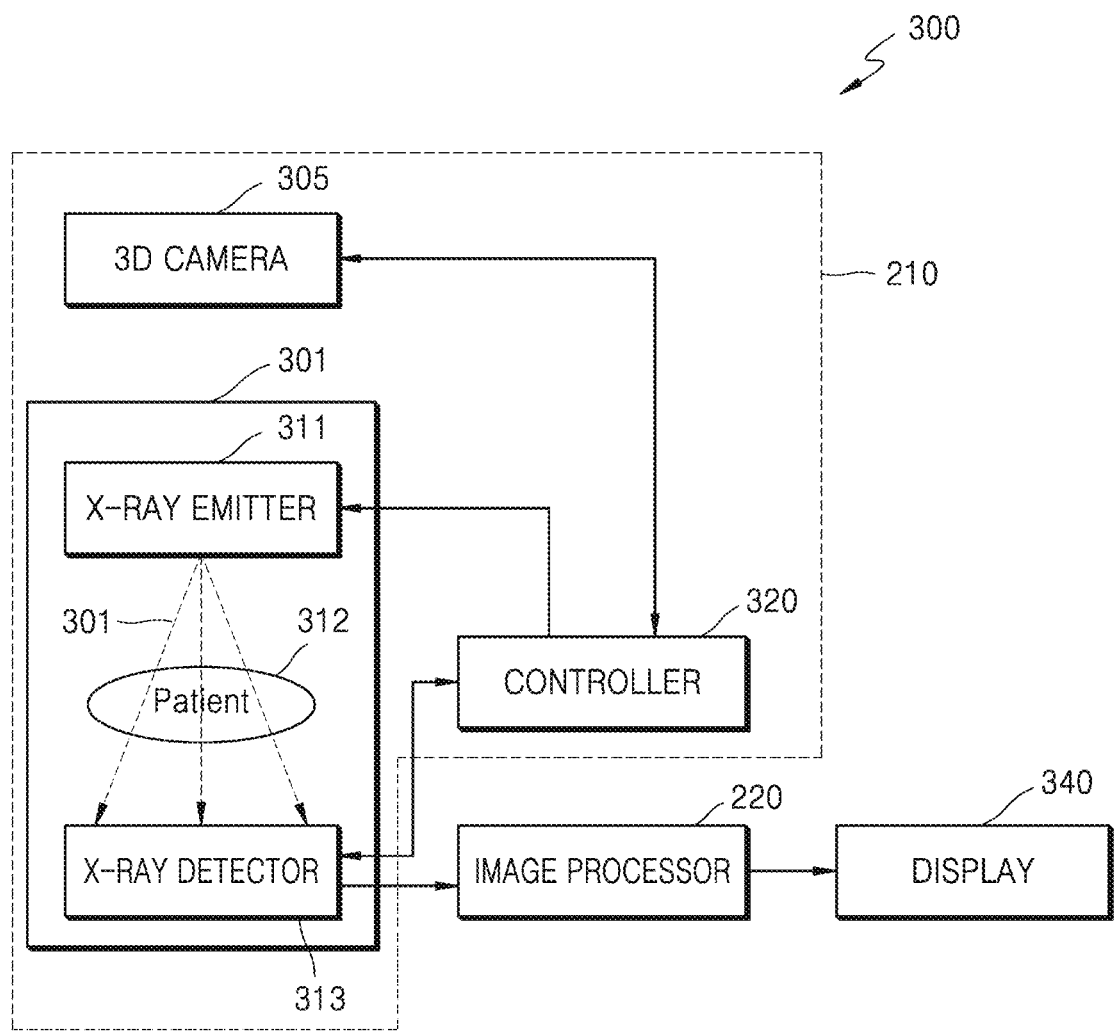
FIG. 3 is a block diagram illustrating an X-ray image processing apparatus according to another embodiment.

FIG. 3 is a block diagram illustrating an X-ray image processing apparatus according to another embodiment. The same elements in an image processing apparatus 300 of FIG. 3 as those of the X-ray image processing apparatus 200 of FIG. 2 are denoted by the same reference numerals. Hence, the same description of the X-ray image processing apparatus 300 of FIG. 3 as that made with reference to FIG. 2 will be omitted.

In the X-ray image processing apparatus 300, the data interface 210 may include a 3D camera 305, a controller 320, and an X-ray image obtainer 301. Also, the controller 320, an X-ray emitter 311, and an X-ray detector 313 of FIG. 3 respectively correspond to the controller 120, the X-ray emitter 110, and the X-ray detector 195 of FIG. 1, and thus the same description as that made with reference to FIG. 1 will be omitted.

Also, the X-ray image processing apparatus 300 may further include a display 340, when compared to the X-ray image processing apparatus 200.

The controller 320 may control operations performed by the X-ray image obtainer 301 to obtain a first X-ray image. Also, the controller 320 may control the 3D camera 305 to obtain 3D information.

In detail, the X-ray emitter 311 and the X-ray detector 313 may perform X-ray emission and X-ray detection operations for generating the first X-ray image under the control of the controller 320. Also, the controller 320 may generate an X-ray image based on an X-ray detection result of the X-ray detector 313. In detail, the controller 320 converts an X-ray detected by the X-ray detector 313 into an electrical signal. The controller 320 may generate the X-ray image based on the converted signal.

Also, the controller 320 includes at least one processor that executes one or more instructions. Each of the at least one processor may perform a predetermined operation by executing at least one of the one or more instructions.

Also, the controller 320 may include an internal memory and at least one processor that executes at least one stored program. In detail, the internal memory of the controller 320 may store one or more instructions. The at least one processor included in the controller 320 may perform a predetermined operation by executing at least one of the one or more instructions stored in the internal memory of the controller 320.

In detail, the controller 320 may include a RAM for storing signals or data input from the outside of the data interface 210 or used as a storage corresponding to various tasks performed by the data interface 210, a ROM for storing a plurality of instructions and/or a control program for controlling the data interface 210, and at least one processor. The processor may include a GPU for performing graphics processing on a video. The processor may be implemented as an SoC in which a core is combined with a GPU. The processor may include a single-core, a dual-core, a triple-core, a quad-core, and a multiple core thereof.

Also, the controller 320 may control an overall operation of the X-ray image processing apparatus 300 in addition to operations of the data interface 210 for obtaining the first X-ray image and/or the 3D information. In detail, at least one processor included in the controller 320 may control operations performed by the X-ray image processing apparatus 300, and may control other elements included in the X-ray image processing apparatus 300 to perform a predetermined operation.

The X-ray image obtainer 301 may directly obtain the first X-ray image by performing X-ray imaging under the control of the controller 320.

The 3D camera 305 may be an imaging apparatus for measuring a 3D depth according to camera technology capable of measuring a 3D depth.

In detail, the 3D camera 305 may be implemented as a stereo camera, a depth camera, or a 3D hybrid camera. The following description relates to an embodiment in which the 3D camera is implemented as a stereo camera. The 3D camera 305 may include a plurality of cameras for obtaining a left eye image and a right eye image. In detail, the 3D camera 305 may include a Left (L) camera for obtaining the left eye image and a Right (R) camera for obtaining the right eye image. The 3D camera may obtain left eye data corresponding to the left eye image and right eye data corresponding to the right eye image by imaging an object 312 that is a subject, under the control of the controller 320.

The controller 320 may obtain 3D information (for example depth information of the object 312) about the object 312 by using the left eye data and the right eye data obtained by the 3D camera 305.

An example of a detailed configuration and a 3D imaging operation of the 3D camera 305 will be described in detail with reference to FIGS. 9 and 10.

The X-ray image obtainer 301 may include the X-ray emitter 311 and the X-ray detector 313. The object 312 may be a body part of a patient. For example, when a musculoskeletal system from among body parts of the patient needs to be diagnosed, the object 312 to which an X-ray is to be emitted may be the patient's shoulder, arm, or leg.

Also, because the X-ray emitter 311 and the X-ray detector 313 of FIG. 3 may correspond to the X-ray emitter 110 and the X-ray detector 195 of FIG. 1, the same description as that made with reference to FIG. 1 will be omitted.

The X-ray emitter 311 generates an X-ray and emits the X-ray to the object 312. In detail, the X-ray emitter 311 may generate an X-ray by applying a high voltage between a cathode and an anode of a vacuum tube included in the X-ray emitter 311. An intensity of an X-ray output from the X-ray emitter 311 may vary according to a tube voltage applied to the vacuum tube, tube current, and a product specification (for example a size of a filament, a size of a focusing electrode, and a distance between the anode and the cathode) of the vacuum tube. Also, because the tube voltage applied to generate the X-ray and the product specification of the vacuum tube have set values or determined values, the intensity of the X-ray output from the X-ray emitter 311 has a known value or a measurable value.

In an embodiment, the X-ray emitter 311 may emit an X-ray having a single energy band to the object 312.

The X-ray detector 313 detects the X-ray emitted from the X-ray emitter 311 and transmitted through the object 312. In detail, the X-ray output from the X-ray emitter 311 may be attenuated while passing through the object 312.

The X-ray detector 313 detects the attenuated X-ray. The controller 320 may generate a first X-ray image based on an X-ray detection result of the X-ray detector 313. In detail, the controller 320 may obtain an intensity of the X-ray passing through the object 312 based on the number of X-ray photons detected by the X-ray detector 313, and may generate the first X-ray image based on the obtained intensity of the X-ray.

Also, the controller 320 may control the image processor 220 to generate the first X-ray image, instead of performing an operation of generating the first X-ray image based on a detection result of the X-ray detector 313. In detail, the controller 320 may control the image processor 220 to generate an X-ray image by transmitting, to the image processor 220, a converted signal obtained by converting the X-ray detected by the X-ray detector 313 into an electrical signal.

In detail, the image processor 220 may generate the first X-ray image based on an X-ray detection result of the X-ray detector 313 under the control of the controller 320. In detail, the X-ray detected by the X-ray detector 313 is converted into an electrical signal. The image processor 220 may generate the first X-ray image based on the converted signal.

That is, a pixel value of the X-ray image may correspond to a size of the electrical signal converted from the X-ray detected by the X-ray detector 313. Also, the image processor 220 may perform pre-processing on the signal generated according to the X-ray detection result of the X-ray detector 313 and may perform post-processing for improving the quality of the X-ray image. Also, types and an order of image processing operations performed by the image processor 220 may be changed.

Also, the image processor 220 may be included in the controller 320. In detail, any of the at least one processor included in the controller 320 may be the image processor 220.

Also, at least one of the at least one processor included in the controller 320 may perform operations (for example an operation of obtaining first information and second information) performed by the image processor 220.

FIG. 3 and the following drawings will be described as relating to embodiments in which an operation of obtaining the first information, the second information, and/or third information by processing the first X-ray image, a scatter correction operation, and a post-processing operation, and any other desired operation are performed by the image processor 220.

The display 340 displays a predetermined screen under the control of the controller 320. In detail, the display 340 may display at least one of the first X-ray image, the first information, the second information, or the third information. Also, the display 340 may display a user interface screen including at least one of the first X-ray image, the first information, the second information, or the third information.

Also, the display 340 may display a screen including an intermediate product or a final result of image processing performed by the image processor 220.

Figure 4:
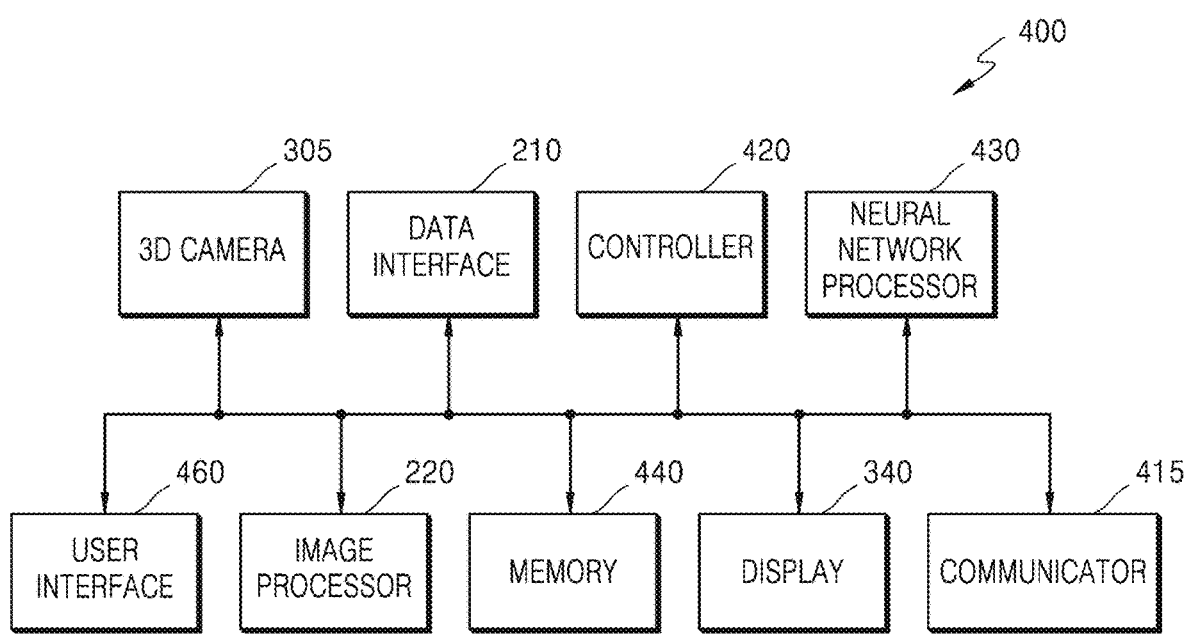
FIG. 4 is a block diagram illustrating an X-ray image processing apparatus according to another embodiment.

FIG. 4 is a block diagram illustrating an X-ray image processing apparatus according to another embodiment. The same elements of an X-ray image processing apparatus 400 of FIG. 4 as those of the X-ray image processing apparatuses 200 and 300 of FIGS. 2 and 3 are denoted by the same reference numerals. Hence, the same description of the X-ray image processing apparatus 400 as that made with reference to FIGS. 2 and 3 will be omitted.

The X-ray image processing apparatus 400 may further include at least one of a user interface 460, a controller 420, a memory 440, the display 340, or the communicator 415, when compared to the X-ray image processing apparatus 200. Also, the X-ray image processing apparatus 400 may further include a neural network processor 430.

The controller 420 may correspond to the controller 320 of FIG. 3.

In detail, the controller 420 may control an overall operation of the X-ray image processing apparatus 400. In detail, at least one processor included in the controller 320 may control operations performed by the X-ray image processing apparatus 400, and may control other elements included in the X-ray image processing apparatus 400 to perform a predetermined operation.

The communicator 415 may transmit/receive data to/from an electronic device through a wired/wireless communication network. In detail, the communicator 415 may transmit/receive data under the control of the controller 420. The communicator 415 may correspond to the communicator 140 of FIG. 1. Also, the electronic device connected through the wired/wireless communication network to the communicator 415 may be the server 151, the medical device 152, or the portable terminal 153 of FIG. 1. Also, the electronic device may be a medical imaging apparatus, e.g., the X-ray apparatus 100 of FIG. 1, which is provided separately from the X-ray image processing apparatus 400.

In detail, when an external electronic device is a medical imaging apparatus, the communicator 415 may receive an actual medical image, e.g., a first X-ray image, obtained by the medical imaging apparatus. Also, the communicator 415 may transmit, to the external electronic device, at least one medical image and/or data including a result obtained by analyzing or diagnosing the medical image. For example, when the image processor 220 obtains second information and third information, the controller 420 may control information obtained through the communicator 415 to be transmitted to the external electronic device.

Also, when a 3D camera is a device separate from the X-ray image processing apparatus 400, the communicator 415 may receive data, e.g., left eye data and right eye data, obtained by imaging an object from the 3D camera. In this case, the controller 420 may obtain 3D information about the object based on the left eye data and the right eye data transmitted from the communicator 415.

The memory 440 may include at least one program necessary to operate the X-ray image processing apparatus 400 or at least one instruction necessary to execute the at least one program. Also, the memory 440 may include at least one processor for performing the above operations.

Also, the memory 440 may store at least one of an X-ray image, information related to the X-ray image, information about a patient, information about an object, or information about an examinee. Also, the memory 440 may store at least one of information, data, or an image generated by the image processor 220. Also, the memory 440 may store at least one of an image, data, or information received from the external electronic device.

The display 340 may display a medical image, a user interface screen, user information, image processing information, and any other information. In detail, the display 340 may display the user interface screen generated under the control of the controller 420. The user interface screen may include the X-ray image, the information related to the X-ray image, and/or information generated by the image processor 220.

The user interface 460 may receive predetermined data or a predetermined command from a user. The user interface 460 may correspond to at least one of the sub-user interface 80 or the input interface 181 of FIG. 1. Also, the user interface 460 may be formed as a touchscreen that is integrally formed with the display 340. As another example, the user interface 460 may include a user input device such as a pointer, a mouse, or a keyboard.

Also, in an embodiment, the X-ray image processing apparatus 400 may perform a computation through a neural network and may obtain a result thereof. For example, the X-ray image processing apparatus 400 may input first information and the first X-ray image through the neural network, may perform a neural network computation, may decompose a first material from among a plurality of materials included in the object, and may generate a 3D image showing a stereoscopic structure of the first material. Also, the X-ray image processing apparatus 400 may input the first information and the first X-ray image through the neural network, may perform a neural network computation, may decompose the first material and a second material from among the plurality of materials included in the object, and may generate a 3D image showing a stereoscopic structure of each of the first material and the second material.

As another example, the X-ray image processing apparatus 400 may input the first X-ray image through the neural network, may perform a neural network computation, and may obtain a first partial image generated by imaging the first material, e.g., soft tissue, and a second partial image generated by imaging the second material, e.g., a bone, by analyzing the first X-ray image.

In detail, the neural network may perform analysis or estimation using input data through an artificial intelligence (AI) system that performs machine learning according to AI technology.

The neural network may optimize and set weight values inside the neural network by training using training data. The neural network self-learns input data in order to derive a result value to be obtained.

In detail, the neural network may be a deep neural network (DNN). Also, a DNN computation may include a convolutional neural network (CNN) computation. In detail, a data recognition model may be implemented through the neural network, and may be trained by using training data. Input data, for example an X-ray image, may be analyzed and classified by using the trained data recognition model, and a specific region (for example a region formed of the first material from among the plurality of materials included in the object) included in the X-ray image may be output.

Also, the computation through the neural network may be performed by the image processor 220. Also, the computation through the neural network may be performed by using at least one of at least one processor included in the image processor 220. Also, the computation through the neural network may be performed by the controller 420. Also, the computation through the neural network may be performed by the neural network processor 430 that is a separate processor. In FIG. 4, the computation through the neural network is performed by the neural network processor 430 that may be a processor separate from the image processor 220 or the controller 420.

In detail, the neural network processor 430 may perform a computation based on the neural network. In detail, a DNN computation may include a CNN computation.

An example of a neural network computation performed by the controller 420, the image processor 220, or the neural network processor 430 will be described in detail with reference to FIG. 19.

Figure 5:
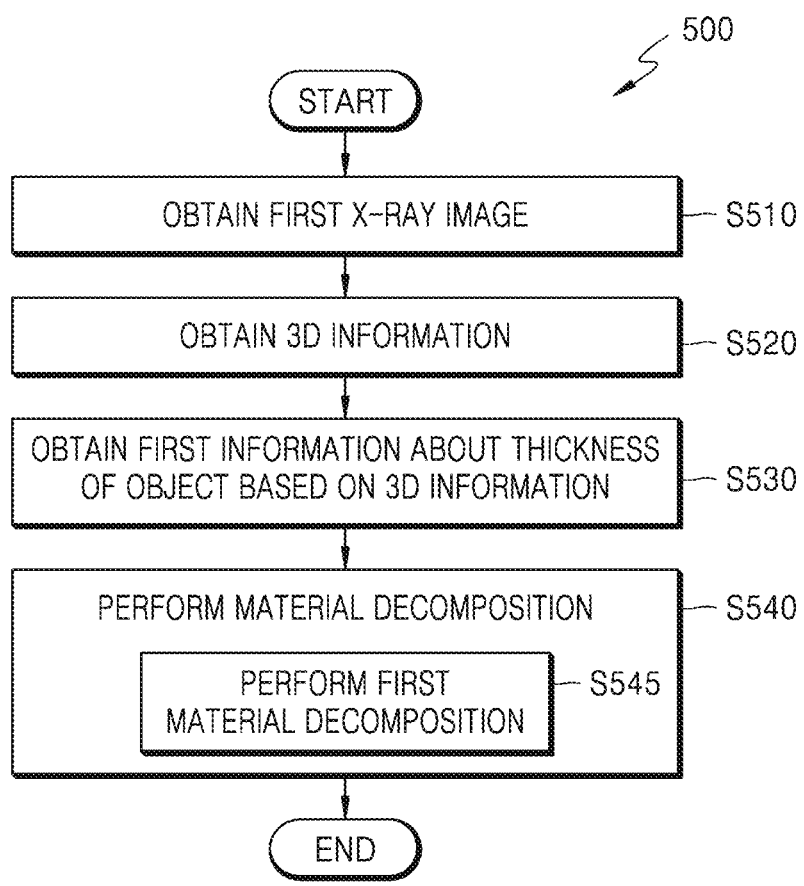
FIG. 5 is a flowchart illustrating an X-ray image processing method according to an embodiment.

FIG. 5 is a flowchart illustrating an X-ray image processing method according to an embodiment. Also, FIG. 5 may be a flowchart for describing operations performed by the X-ray image processing apparatus 200, 300, or 400 according to an embodiment described with reference to FIGS. 2 through 4.

An X-ray image processing method 500 according to an embodiment may be performed by the X-ray image processing apparatus 200, 300, or 400 according to an embodiment described with reference to FIGS. 2 through 4. Accordingly, each operation of the X-ray image processing method 500 may be performed by each element of the X-ray image processing apparatus 200, 300, or 400, and the X-ray image processing method 500 may have the same characteristics as those of the X-ray image processing apparatus 200, 300, or 400. Accordingly, the same description of the X-ray image processing method 500 as that made with reference to FIGS. 1 through 4 will be omitted.

An example of the X-ray image processing method 500 will be described in detail with reference to the medical image processing apparatus 300 of FIG. 3.

Referring to FIG. 5, in operation S510, the X-ray image processing method 500 obtains a first X-ray image. The first X-ray image is an X-ray image obtained by imaging an object formed of a plurality of materials including a first material and a second material. Operation S510 may be performed by the data interface 210 under the control of the controller 320.

The X-ray image (which may be referred to as the 'first X-ray image') obtained by imaging the object is a medical image obtained by imaging the inside of the object based on the number of X-ray photons transmitted through the object. An example intensity of the X-ray emitted to the object and transmitted through the object will be described in detail with reference to FIG. 8.

Figure 8:
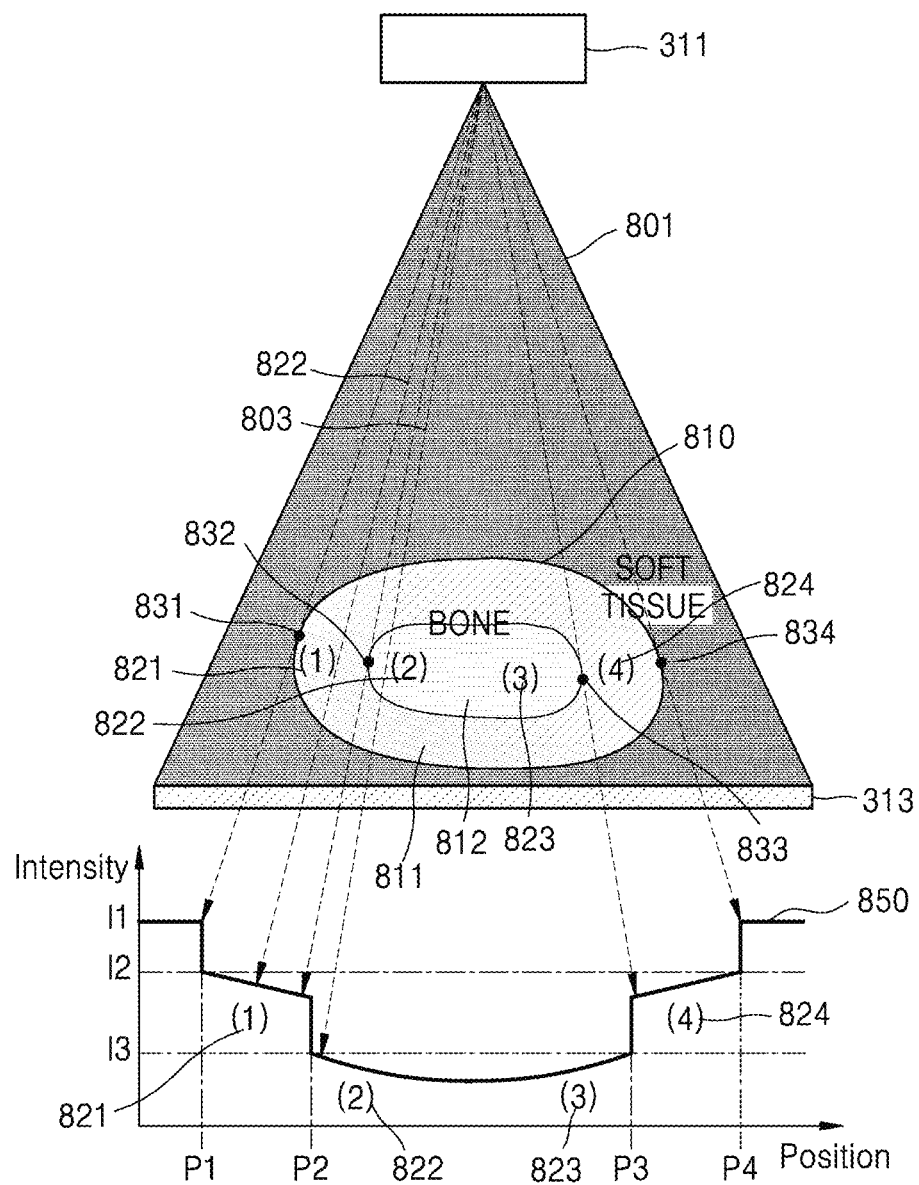
FIG. 8 is a view for describing an operation of obtaining an X-ray image according to an embodiment.

FIG. 8 is a view for describing an operation of obtaining an X-ray image according to an embodiment. In detail, FIG. 8 is a view for describing an operation of performing X-ray imaging by using the X-ray image obtainer 301. The same elements in FIG. 8 as those of FIG. 3 are denoted by the same reference numerals. Accordingly, the same description of FIG. 8 as that made with reference to FIG. 3 will be omitted.

An X-ray image of a patient's arm may be captured in order to diagnose a disease in the patient's predetermined body part, e.g., the patient's musculoskeletal system. FIG. 8 will be described as relating to an embodiment in which the object is the patient's arm, as in the above example.

The object may be formed of a plurality of different materials. In detail, the arm may include an arm bone and soft tissue surrounding the arm bone. The following description relates to an embodiment in which a first material is soft tissue and a second material is a bone. In the following equations, 'S' denotes soft tissue, and 'B' denotes a bone.

Referring to FIG. 8, an X-ray 801 is emitted to an object 810 to obtain a first X-ray image. In detail, the X-ray emitter 311 outputs an X-ray having an intensity $I_o$ to the object 810. The X-ray detector 313 detects an X-ray having an intensity I that is an X-ray passing through the object 810. The first X-ray image may be generated based on the X-ray detected by the X-ray detector 313.

FIG. 8 illustrates a cross-section of the arm, that is, a vertical cross-section of the object in an X-ray emission direction. In detail, the object 810 may include a bone 812 and soft tissue 811 surrounding the bone 812.

Referring to FIG. 8, a graph 850 is a graph showing an intensity of an X-ray detected by the X-ray detector 313. In detail, the X-axis of the graph 850 represents a position in the vertical cross-section of the object 810. Also, the Y-axis represents the intensity I of the X-ray detected by the X-ray detector 313.

An X-ray emitted to the object is partially absorbed by the object and partially transmitted through the object. A degree of transmission of the X-ray varies according to a type of a material in the object.

Referring to FIG. 8, an intensity of an X-ray not transmitted through the object may be I1. The intensity I1 may be the same as the intensity $I_o$ of the X-ray emitted by the X-ray emitter 311. The intensity of the X-ray transmitted through the object 810 starts to be reduced from a boundary 831 of the object 810. For example, the intensity of the X-ray detected by the X-ray detector 313 is reduced from I1 at the boundary 831 of the object 810 to I2. In the graph 850, a position corresponding to the boundary 831 of the object 810 is denoted by P1. The reduction in the intensity of the X-ray occurs because a part of the X-ray is absorbed by the object 810 while being transmitted through the object 810. Such X-ray absorption characteristics may be referred to as X-ray attenuation characteristics.

As described above, the X-ray absorption characteristics may vary according to internal materials of the object 810. For example, X-ray attenuation when passing through the bone 812 may be greater than X-ray attenuation when passing through the soft tissue 811. Also, as a thickness of the object 810 through which the X-ray is transmitted increases, X-ray attenuation may increase. Also, as internal materials change, a degree of X-ray absorption or attenuation also changes.

Referring to FIG. 8, a region 821 (1) of the object 810 is a region where only the soft tissue 811 exists. A region 822 (2) and a region 823 (3) of the object 810 are regions where the soft tissue 811 and the bone 812 exist in an overlapping manner and an X-ray 803 output from the X-ray emitter 311 is transmitted through both the bone 812 and the soft tissue 811. A region 824 (4) of the object 810 is a region where only the soft tissue 811 exists.

An X-ray 802 transmitted through the region 821 (1) of the object 810 may have the same intensity as that in an interval between the position P1 and a position P2 of the graph 850. A degree of X-ray absorption or attenuation at the boundary 832 between the soft tissue 811 and the bone 812 sharply changes. In the graph 850, a position corresponding to the boundary 832 between the soft tissue 811 and the bone 812 is denoted by P2. Accordingly, an X-ray transmitted through the bone 812 and detected may have the same intensity as that in an interval between the position P2 and a position P3.

Also, a degree of X-ray absorption or attenuation at a boundary 833 between the bone 812 and the soft tissue 811 sharply changes. In the graph 850, a position corresponding to the boundary 833 between the bone 812 and the soft tissue 811 is denoted by P3. Accordingly, an X-ray transmitted through the soft tissue 811 and detected may have the same intensity as that in an interval between the position P3 and a position P4.

In detail, X-ray absorption characteristics may be defined as in [Equation 1].

$$I = I_o e^{-\Sigma(\mu_j^L(E) \times t_j)}$$ [Equation 1]

I denotes an intensity of an X-ray transmitted through an object and detected, $I_o$ denotes an intensity of an X-ray emitted to the object (for example an intensity of an X-ray generated by the X-ray emitter 311 and output to the object 312), and $\mu_j^L$ denotes a linear attenuation coefficient indicating a degree to which an X-ray having an energy band E is attenuated while being transmitted through a j material. The linear attenuation coefficient may vary according to a material. For example, linear attenuation coefficients of soft tissue and a bone have different values. $t_j$ denotes a thickness of the j material. In detail, t may refer to a transmission thickness (or a projection thickness) that is a path through which an X-ray is transmitted through the object. That is, the transmission thickness may refer to a length of a path through which the X-ray is transmitted in the object. According to [Equation 1], a degree of attenuation of an X-ray increases as the transmission thicknesses increases.

Because the intensities I and $I_o$ respectively correspond to the X-ray transmitted through the object and detected and the X-ray output to the object during X-ray imaging, the intensities I and $I_o$ may be immediately known as a result of setting and X-ray detection during the X-ray imaging of the X-ray apparatus 100.

In detail, the intensity I may be a signal value generated by electrically converting the number of X-ray photons detected by the X-ray detector 313. For example, the intensity I may be a voltage value generated by electrically converting the number of X-ray photons detected by the X-ray detector 313. In an embodiment, the intensity I may be a current value generated by electrically converting the number of X-ray photons detected by the X-ray detector 313.

Also, the intensities I and $I_o$, may be obtained by using corresponding pixel values in an X-ray image. That is, the intensity I may correspond to a pixel value of a designated region in the X-ray image, and the intensity $I_o$ may correspond to a pixel value corresponding to an output X-ray, that is, a pixel value of a region where the object does not exist in the X-ray image. Also, a pixel value of the X-ray image may be represented as a value corresponding to the number of X-ray photons detected by the X-ray detector 313 of FIG. 3. For example, when an X-ray passes through the bone and attenuation of the X-ray increases, the number of X-ray photons passing through the bone decreases. As another example, attenuation of the X-ray passing through the soft tissue is less than attenuation of the X-ray passing through the bone. Hence, an intensity of a corresponding X-ray may be obtained by using a pixel value in the X-ray image.

In an embodiment, a first partial region where only the soft tissue is imaged may correspond to the region 821 (1), and a second partial region where the soft tissue and the bone are imaged in an overlapping manner may correspond to the region 822 (2).

Also, [Equation 1] may be modified to [Equation 2].

$$J = -\log\left[\frac{I}{I_o}\right] = \sum (\mu_j^L(E) \times t_j) \qquad \text{[Equation 2]}$$

Also, when an X-ray passes through an object (for example a patient's specific body part) existing in a 3D space, a degree of X-ray attenuation is proportional to a density of a material existing in the space, and thus $\mu_j^L$ may be expressed as $\mu_j \rho_j$. $\mu_j$ denotes a mass attenuation coefficient, and $\rho_j$ denotes a density value of a j material. Hereinafter, the mass attenuation coefficient will be simply referred to as an 'attenuation coefficient'. That is, when an X-ray passes through an object having a 3D structure, a degree of X-ray attenuation may be represented as a value obtained by multiplying an attenuation coefficient of the j material by a density of the j material. Accordingly, [Equation 1] may be modified to [Equation 3].

$$I = I_o e^{-\Sigma(\mu_j \rho_j \times t_j)} \qquad \text{[Equation 3]}$$

[Equation 3] is represented using a sigma that is a summation of $\mu_j \rho_j t_j$ that is a value obtained by multiplying $\mu_j \rho_j$ by $t_j$. This indicates that when an X-ray is transmitted through an object comprised by a plurality of materials that exist in an overlapping manner, the X-ray is attenuated inverse-exponentially with respect to a value obtained by adding $\mu_j \rho_j t_j$ values of the plurality of materials.

In an embodiment, X-ray absorption characteristics may be used in material decomposition in operation S540.

Referring again to FIG. 5, in operation S520, the X-ray image processing method 500 obtains 3D information. The 3D information that is information obtained by imaging the object by using a 3D camera may include information about a stereoscopic structure of the object. In detail, the 3D information may include depth information about the object. In detail, a depth may correspond to a distance value indicating how far the object is separated from the 3D camera. Operation S520 may be performed by the data interface 210 under the control of the controller 320. An example of the 3D information will be described in detail with reference to FIG. 9.

Figure 9:
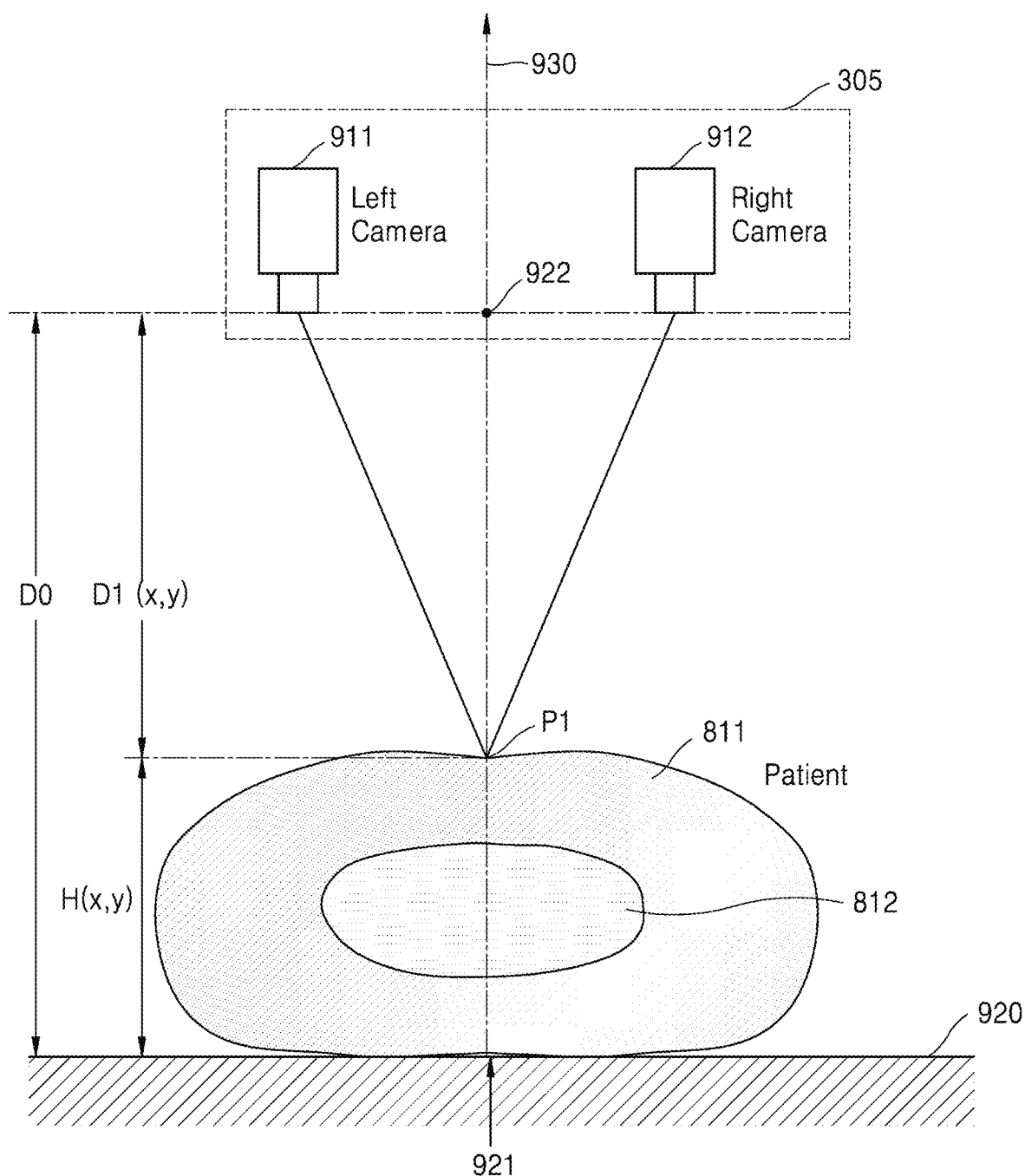
FIG. 9 is a view for describing an operation of obtaining three-dimensional (3D) information according to an embodiment.

FIG. 9 is a view for describing an operation of obtaining 3D information according to an embodiment. Also, FIG. 9 will be described as relating to an embodiment in which the object 810 of FIG. 8 which is a subject to be imaged by a stereo camera is a patient's arm.

The 3D camera 305 may be implemented as a stereo camera. In FIG. 9, the 3D camera 305 is a stereo camera. Referring to FIG. 9, the 3D camera 305 includes a left eye camera 911 for obtaining a left eye image and a right eye camera 912 for obtaining a right eye image. Also, when a position where the X-ray emitter 311 outputs an X-ray is 922, the left eye camera 911 and the right eye camera 912 may be located at front-left and front-right sides of the position 922 of the X-ray emitter 311. Also, the stereo camera illustrated in FIG. 9 is merely an example of the 3D camera 305, and three or more cameras for calculating more accurate depth information may be used to obtain a multi-view image.

When a distance between the left eye camera 911 and the right eye camera 912 and a distance between a point (for example P1) of an object in the left eye image obtained through the left eye camera 911 and a point (for example P1) of the object in the right eye image obtained through the right eye camera 912 are known, a depth value that is a distance from the 3D camera 305 to a surface of the object 810 may be obtained.

In an embodiment, 3D information may include the left eye image and the right eye image respectively obtained by the left eye camera 911 and the right eye camera 912. The left eye image and the right eye image may be collectively referred to as a stereo image. A difference between the same points in the object in the stereo image may be referred to as binocular parallax. Also, the 3D information may include raw data obtained by the left eye camera 911 and raw data obtained by the right eye camera 912. The raw data may refer to electrical signal values sensed by an imaging sensor included in the 3D camera 305. Also, the raw data obtained by the left eye camera 911 and the raw data obtained by the right eye camera 912 may be collectively referred to as stereo data.

Also, in an embodiment, a camera distance that is a distance between the left eye camera 911 and the right eye camera 912 in the 3D camera 305 may be a known value. That is, the controller 320 may already know the camera distance in the 3D camera.

Also, the 3D camera 305 may not image the inside of the object 810, and may three-dimensionally image a surface of the object close to the 3D camera 305, for example the surface of the object located within or outside a distance D1(x, y). Accordingly, the 3D camera 305 may obtain 3D information for obtaining a depth value of the surface of the object.

Also, the 3D camera 305 may be implemented as a depth camera. In this case, the depth camera may include an infrared sensor for obtaining depth information of the subject and a color camera. For example, two color cameras may be installed at front-left and front-right sides of the X-ray emitter 311 and an infrared sensor may be installed in the middle between the two color cameras. The depth camera may obtain depth information by using time-of-flight (TOF) technology. The TFT technology refers to the measurement of a distance by calculating a time taken for an infrared signal to be reflected back to the subject.

When the 3D camera 305 is implemented as a depth camera, 3D information obtained according to an embodiment may include a sensing value of an infrared sensor. In an embodiment, the 3D information may include a distance value obtained by the infrared sensor.

The following description relates to an embodiment in which the 3D information is a camera distance between a stereo image and the 3D camera 305.

Referring again to FIG. 5, in operation S530, the X-ray image processing method 500 obtains first information about a thickness of the object based on the 3D information obtained in operation S520. Operation S530 may be performed by the image processor 220.

In detail, the image processor 220 may calculate depth information of the subject by performing stereo matching on a camera distance and binocular parallax in the stereo image. The depth information of the subject may be D1(x, y) that is a distance from the 3D camera 305 to a point (for example P1) of the surface of the object. Also, a distance D0 from the 3D camera 305 to a surface, e.g., a surface of a table 920, on which the object is located is a known value or a measurable value. Hence, at the point P1 on the surface of the object, a thickness of the object may be D0−D1(x, y)=H(x, y).

Here, (x, y) that are coordinates for specifying a position of the object may vary according to settings of the X-ray image processing apparatus 300 or a user. In FIG. 9, regarding coordinates for specifying a position on the surface (for example a surface perpendicular to a straight line 930) of the table 920, a line along the table 920 becomes the x-axis and a line perpendicular to the surface of the table 920 becomes the y-axis. Accordingly, in FIG. 9, the origin (0, 0) may be a position 921.

As described above, the image processor 220 may obtain a total thickness of the object according to each position based on the 3D information obtained by the 3D camera 305. For example, the image processor 220 may calculate H(x, y) that is a thickness of the object at the point P1 by using D1(x, y) that is a depth value at the point P1. Here, H(x, y) may refer to a thickness of the object corresponding to a position on the surface of the object corresponding to the coordinates (x, y).

Also, a thickness of the object included in the first information may be a vertical thickness like H(x, y) of FIG. 9. In an embodiment, the first information may refer to a transmission thickness that is a length of a transmission path of an X-ray transmitted through the object. The following description relates to an embodiment in which information about a thickness of the object included in the first information is a transmission thickness of the object.

An example of operation S530 of obtaining the first information will be described in detail with reference to FIGS. 10 and 11.

Figure 10:
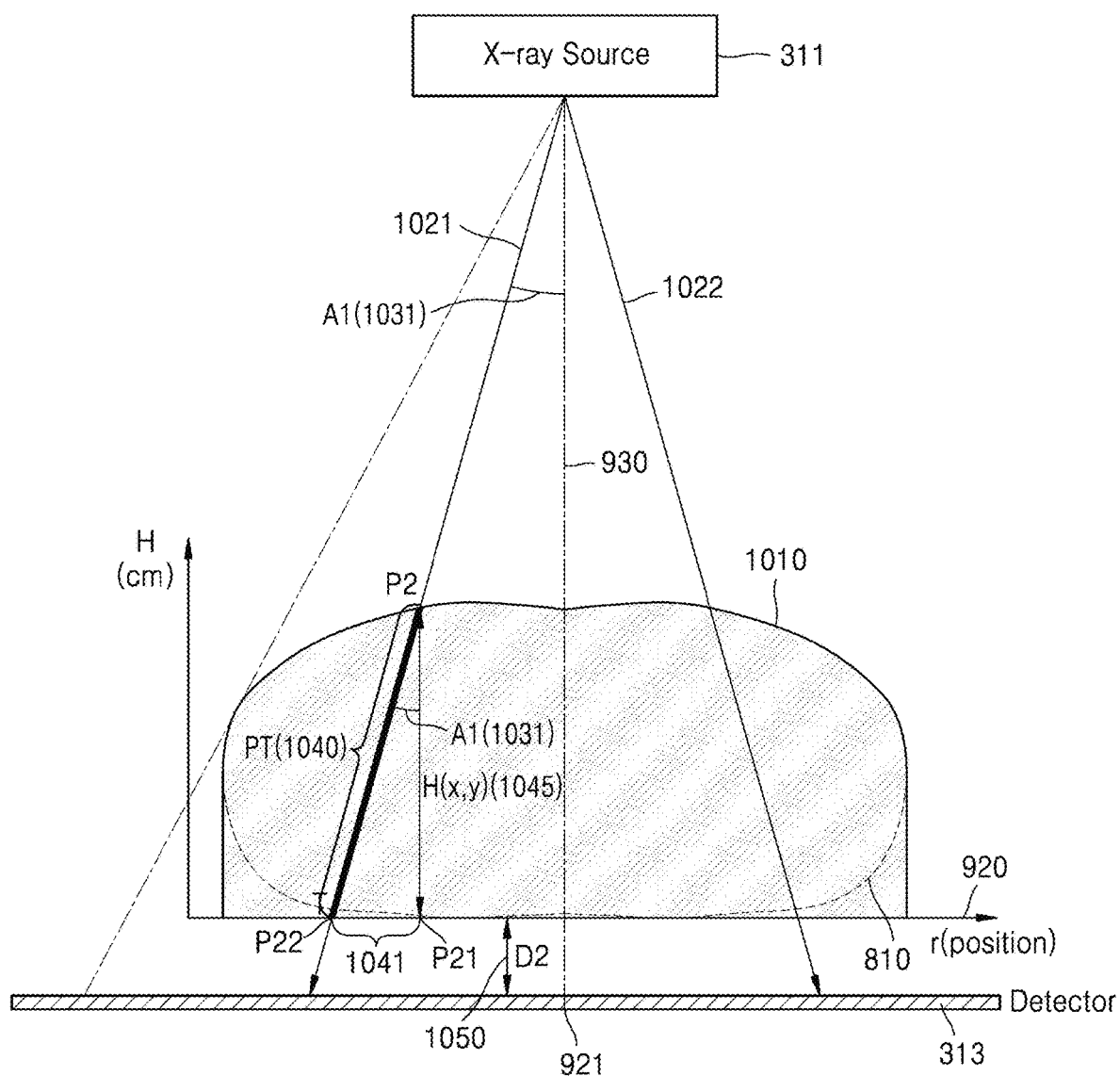
FIG. 10 is a view for describing an operation of obtaining first information based on 3D information according to an embodiment.

FIG. 10 is a view for describing an operation of obtaining first information based on 3D information according to an embodiment. In detail, FIG. 10 is a view for describing a transmission thickness of an object. In FIG. 10, the same elements as those of FIGS. 8 and 9 are denoted by the same reference numerals. Accordingly, the same description as that made with reference to FIGS. 8 and 9 will be omitted.

Figure 11:
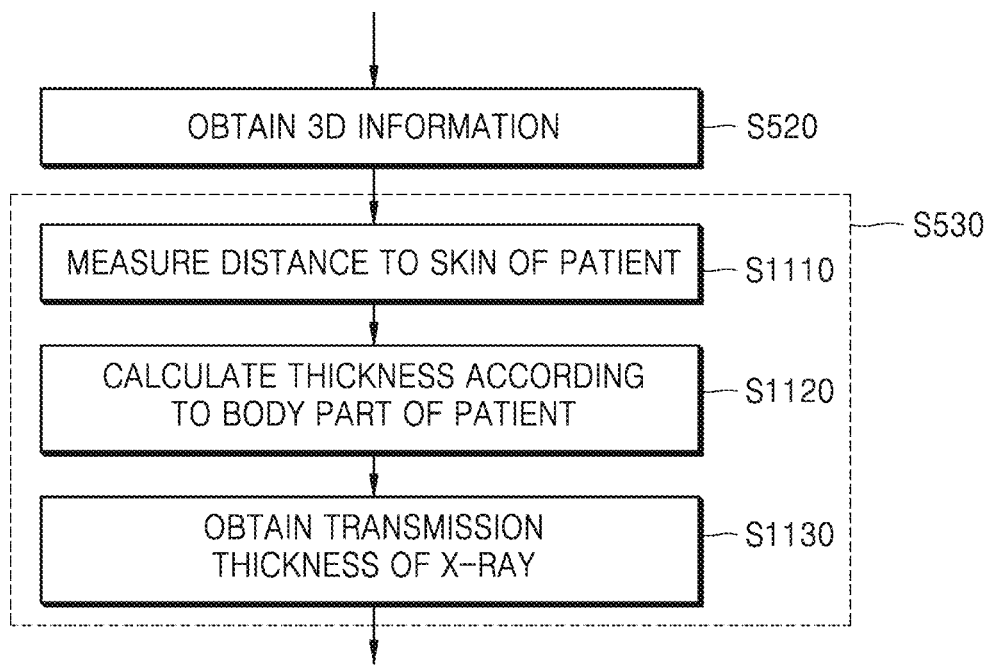
FIG. 11 is a diagram for describing an operation of obtaining first information based on 3D information according to another embodiment.

FIG. 11 is a diagram for describing an operation of obtaining first information based on 3D information according to another embodiment. In FIG. 11, the same elements as those of FIG. 5 are denoted by the same reference numerals. Accordingly, the same description of operations of FIG. 11 as that made with reference to FIG. 5 will be omitted.

Referring to FIG. 11, in operation S530, first information including depth information about a surface of an object may be obtained based on 3D information about the object that is obtained by the 3D camera 305.

In detail, referring to FIG. 11, operation S530 of obtaining the first information may include operation S1110 in which a distance from the 3D camera 305 to the surface of the object is obtained based on the 3D information. As described with reference to FIG. 9, depth information of a subject may be D1(x, y) that is a distance from the 3D camera 305 to a point (for example P1) on the surface of the object. Accordingly, a distance from the 3D camera 305 to the surface of the object may be measured based on the 3D information.

In operation S1120, the image processor 220 may obtain the first information about a thickness of the object based on the distance from the 3D camera 305 to the surface of the object. Also, the image processor 220 may obtain H(x, y) that is a thickness of the object at any position corresponding to the surface of the object. That is, the image processor 220 may obtain a thickness of the object at any position along the x-axis of FIG. 9.

In operation S1130, the image processor 220 may obtain a transmission thickness PT 1040 of an X-ray by using the thickness H(x, y) of the object.

An operation of obtaining the transmission thickness PT 1040 will be described in detail.

Referring to FIG. 10, first information may include distance values of a line 1010 that is depth information about a surface of an object. That is, because the 3D camera 305 images the surface of the object located on an imaging surface of the camera 305, a depth value of a surface of the object (for example, a surface of the object close to the table 920) located outside the imaging surface of the camera 305 may not be obtained by using information obtained by the 3D camera 305.

Also, referring to FIG. 10, the X-ray detector 313 detects an X-ray transmitted through the object. The X-ray detector 313 may be located on a plane parallel to the table 920. In detail, the X-ray detector 313 may be located on a plane parallel to the table 920 and different from a surface of the table 920. That is, although the X-ray detector 313 is spaced apart by a distance D2 from the object 810 in FIG. 10, the X-ray detector 313 may be located on a surface contacting the object 810. When the X-ray detector 313 is located on the surface contacting the object 810, the distance D2 may be 0 (D2=0). Also, the distance D2 may vary according to product specifications or settings of the X-ray image obtainer 301 or a user.

Referring to FIG. 10, when the X-ray emitter 311 transmits an X-ray through the object 810, a distance of the X-ray transmitted through the object 810 may be referred to as a transmission thickness (for example, to in [Equation 1]). In detail, when the X-ray emitter 311 emits an X-ray at the position 922, a transmission thickness of an X-ray 1021 transmitted through a position P2 of the object 810 may be PT 1040.

As described with reference to FIG. 9, the image processor 220 may obtain H(x, y) that is a thickness 1045 of the object by using 3D information obtained by using a 3D camera. When the thickness H(x, y) of the object is known, the image processor 220 may obtain the transmission thickness PT 1040 by using [Equation 4].

$$PT = H \times \cos(A1) \qquad \text{[Equation 4]}$$

In [Equation 4], PT denotes the transmission thickness 1040, and H denotes the thickness 1045 of the object included in the first information. Also, A1 denotes an angle 1031 at which an X-ray is emitted. For the straight line 930 that is a projection path of an X-ray passing through the origin (0, 0) 921 of coordinates (x, y), the angle A1 1031 may have a value of 0. Also, a value of the angle A1 may be a known value or a measurable value.

In [Equation 4], the thickness H may be obtained by using the first information, and the angle A1 has a known value or a measurable value. Accordingly, the transmission thickness PT 1040 of the object may be obtained by using the first information and [Equation 4].

Also, when the object is formed of a first material, e.g., soft tissue, and a second material, e.g., a bone, the transmission thickness PT ($=t_j$) may be represented as a sum of a transmission thickness $t_B$ of the bone and a transmission thickness $t_S$ of the soft tissue.

That is, the transmission thickness PT may be defined as in [Equation 5].

$$t_j = PT = t_s + t_B \qquad \text{[Equation 5]}$$

Also, when the first material is soft tissue and the second material is a bone, $t_j$ of [Equation 3] may be applied to [Equation 5] to obtain [Equation 6].

$$J = -\log\left[\frac{I}{Io}\right] = \mu_S \rho_S t_S + \mu_B \rho_B t_B \qquad \text{[Equation 6]}$$

Also, [Equation 5] may be modified to [Equation 7].

$$t_s = PT - t_B \qquad \text{[Equation 7]}$$

When [Equation 7] is applied to [Equation 6], [Equation 6] may be modified to [Equation 8].

$$J = -\log\left[\frac{I}{Io}\right] = (\mu_B \rho_B - \mu_S \rho_S) t_B + \mu_S \rho_S PT \qquad \text{[Equation 8]}$$

In [Equation 8], an attenuation coefficient $\mu_S$ of the soft tissue, a density $\rho_S$ of the soft tissue, an attenuation coefficient $\mu_B$ of the bone, and a density $\rho_B$ of the bone may be known values. Because I is an intensity of an X-ray transmitted through the object and detected and Io is an intensity of an X-ray emitted to the object (for example an intensity of an X-ray generated by the X-ray emitter 311 and output to the object 312), the intensities I and Io are known values or measurable values.

Accordingly, in [Equation 8], unknown values are a transmission thickness of the bone and the transmission thickness PT of an X-ray, and the transmission thickness PT may be obtained by using the first information. Accordingly, when the transmission thickness PT obtained from the first information is applied to [Equation 8] showing X-ray absorption characteristics, the transmission thickness $t_B$ of the bone may be obtained.

Also, when the transmission thickness PT is known and the transmission thickness $t_B$ of the bone is obtained, the transmission thickness $t_S$ of the soft tissue may be obtained by using [Equation 7].

Also, when [Equation 5] is modified to indicate the transmission thickness of the bone, [Equation 8] may be represented as an equation using the transmission thickness $t_S$ of the soft tissue. Accordingly, the transmission thickness $t_S$ of the soft tissue may be obtained earlier than the transmission thickness $t_B$ of the bone.

As described above, when the intensities I and Io that are obtainable from the first X-ray image and the first information are used and [Equation 8] showing X-ray absorption characteristics is used, a thickness distribution of the soft tissue or a thickness distribution of the bone included in the object over an entire region of the object may be obtained.

Referring back to FIG. 5, in operation S540, material decomposition of at least one material of the object may be performed based on the first information and the first X-ray image. That is, in operation S540, second information related to a stereoscopic structure of the first material may be obtained by decomposing the first material from the object based on the first information and the first X-ray image. Operation S540 may be performed by the image processor 220.

Material decomposition may refer to a process of obtaining information about each of different materials included in the object. In detail, material decomposition may refer to a process of obtaining information about a thickness, a volume, a shape, a geometric structure, and any other aspect of at least one material from among a plurality of materials included in the object.

In detail, operation S540 may include operation S545 in which material decomposition of the first material of the object is performed. Also, operation S540 may include performing material decomposition on the second material of the object.

In a X-ray image processing apparatus and X-ray image processing method according to the related art, when an object is formed of a plurality of materials, in order to obtain information about each of the plurality of different materials included in the object, a plurality of X-ray images obtained by emitting X-rays corresponding to a plurality of energy bands to the object were required. This is because [Equation 1] showing X-ray absorption characteristics is represented using a sigma that is a summation of the plurality of materials included in the object. The X-rays corresponding to the plurality of energy bands may be referred to as dual energy X-rays or multi-energy X-rays.

For example, in related art, in order to measure thicknesses of a bone and soft tissue, both an X-ray image obtained by emitting an X-ray having a low energy band to the object and an X-ray image obtained by emitting an X-ray having a high energy band to the object had to be used. Accordingly, in order to obtain thicknesses of the plurality of materials in the object, X-ray imaging had to be performed multiple times. Accordingly, the amount of X-rays emitted to a patient had to increase.

Also, in related art, information about a stereoscopic structure of the object may not be obtained from one X-ray image having a single energy band. This is because due to X-ray image characteristics, the object may be two-dimensionally imaged by projecting X-rays to a front surface of the object, and information about a vertical cross-section of the front surface of the object may not be obtained.

However, according to an embodiment, the second information related to the stereoscopic structure of the first material may be obtained from 3D information (for example, information obtained by the 3D camera) that may be obtained without X-ray emission and one X-ray image. Accordingly, information about each of different materials may be obtained more rapidly and easily. Also, because material decomposition of a specific material may be performed by performing X-ray imaging only once, the amount of X-rays emitted to the object may be minimized.

Figure 6:
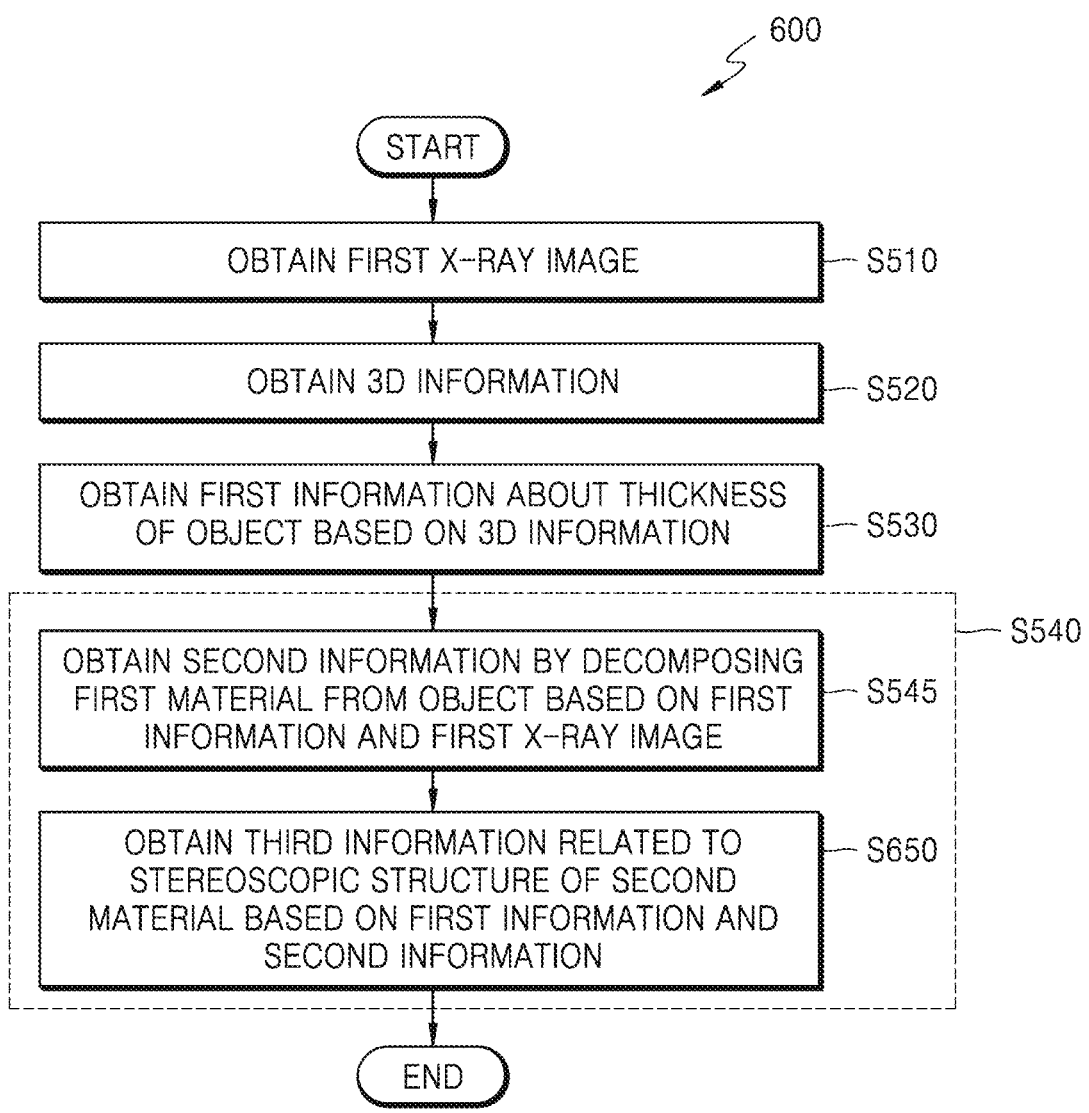
FIG. 6 is a flowchart illustrating an X-ray image processing method according to another embodiment.

FIG. 6 is a flowchart illustrating an X-ray image processing method according to an embodiment. An X-ray image processing method 600 according to an embodiment may be performed by the X-ray image processing apparatus 200, 300, or 400 according to an embodiment described with reference to FIGS. 2 through 4. Accordingly, each operation of the X-ray image processing method 600 may be performed by each element of the X-ray image processing apparatus 200, 300, or 400. Also, the same elements in the X-ray image processing method 600 of FIG. 10 as those of the X-ray image processing method 500 of FIG. 5 are denoted by the same reference numerals. Hence, the same description of the X-ray image processing method 600 as that made with reference to FIGS. 1 through 5 will be omitted.

An example of the X-ray image processing method 600 will be described in detail with reference to the medical image processing apparatus 300 of FIG. 3.

The X-ray image processing method 600 may further include operation S650, in addition to operations of the X-ray image processing method 500.

In detail, in operation S650, the X-ray image processing method 600 may obtain third information related to a stereoscopic structure of the second material based on the first information and the second information. Operation S650 may be performed by the image processor 220.

In detail, in operation S650, when the second information is obtained by decomposing the first material, the second material may be decomposed by using the decomposed first material.

As described above, when [Equation 5] is modified to indicate the transmission thickness of the bone, [Equation 8] may be represented as an equation using the transmission thickness $t_S$ of the soft tissue. Accordingly, the transmission thickness $t_S$ of the soft tissue may be obtained earlier than the transmission thickness $t_B$ of the bone. Once the second information that is information about the transmission thickness $t_S$ of the soft tissue is obtained, the third information that is information about the transmission thickness $t_B$ of the bone may be obtained by applying the transmission thickness $t_S$ of the soft tissue to [Equation 5].

In the X-ray image processing method 600, operation S545 may be referred to as a first material decomposition operation because operation S545 is a step of performing material decomposition on the first material. Also, in the X-ray image processing method 600, operation S650 may be referred to as a second material decomposition operation because operation S650 is a step of performing material decomposition on the second material.

Figure 7:
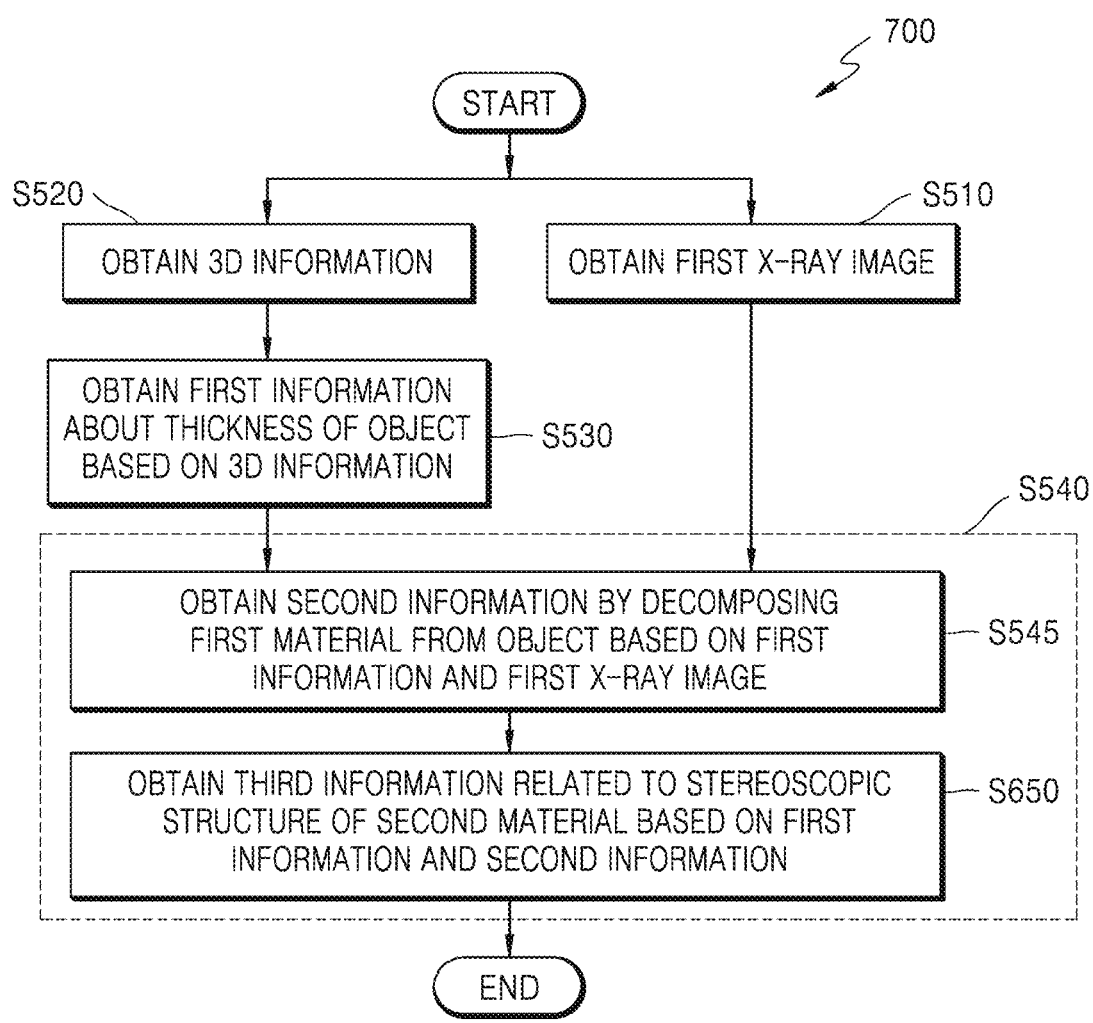
FIG. 7 is a flowchart illustrating an X-ray image processing method according to another embodiment.

FIG. 7 is a flowchart illustrating an X-ray image processing method according to an embodiment. Also, the same elements in an X-ray image processing method 700 of FIG. 7 as those of the X-ray image processing method 600 of FIG. 6 are denoted by the same reference numerals. Hence, the same description of the X-ray image processing method 700 as that made with reference to FIGS. 1 through 6 will be omitted.

Referring to FIG. 7, operation S520 in which 3D information is obtained and operation S510 in which a first X-ray image is obtained may be performed in parallel or regardless of a time order. That is, although operation S510 in which an X-ray image is obtained is first performed and then operation S520 in which 3D information is obtained is performed for convenience of explanation, operation S510 and operation S520 may be performed regardless of a time order.

Other elements in the X-ray image processing method 700 may be the same as those of the X-ray image processing method 600.

Figure 12:
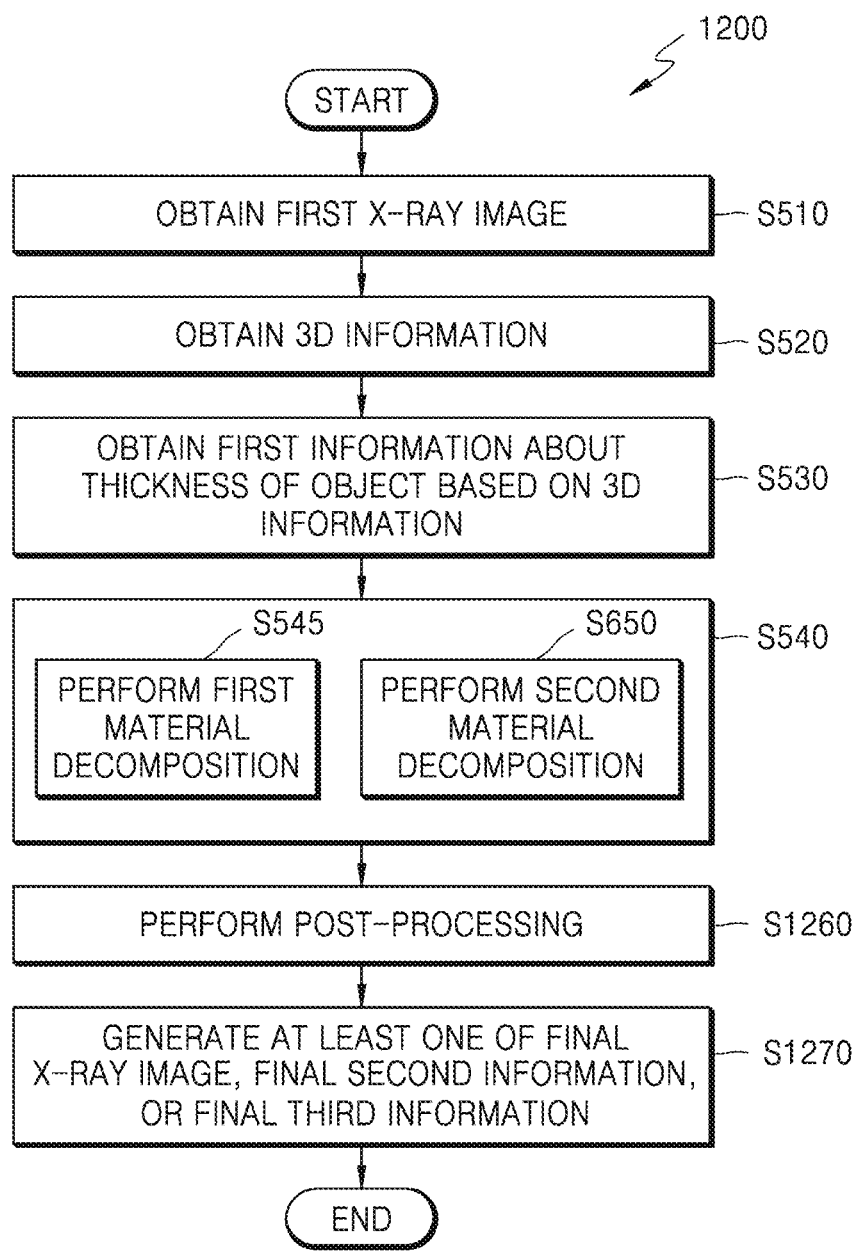
FIG. 12 is a flowchart illustrating an X-ray image processing method according to another embodiment.

FIG. 12 is a flowchart illustrating an X-ray image processing method according to another embodiment. Also, the same elements in an X-ray image processing method 1200 of FIG. 12 as those of the X-ray image processing method 600 of FIG. 6 are denoted by the same reference numerals. Hence, the same description of the X-ray image processing method 1200 as that made with reference to FIGS. 1 through 11 will be omitted.

The X-ray image processing method 1200 may further include operation S1260 in which post-processing is performed on the first X-ray image, after operation S540 of the X-ray image processing method 600. Operation S1260 may be performed by the image processor 220.

The post-processing may include removal of a noise component or a noise signal included in at least one of the first X-ray image or a stereo image or improvement of image uniformity to improve reading accuracy. For example, when the post-processing is performed on the first X-ray image, the post-processing may include removal or reduction of scattering noise caused by a scattered X-ray generated during X-ray imaging.

Also, the post-processing may include generating final second information and final third information based on the second information and the third information. For example, the post-processing may include generating the final second information indicating a stereoscopic structure of the first material from the second information indicating the thickness of the first material so that the user may easily read the object imaged in the first X-ray image. Also, the post-processing may include generating the final second information indicating a stereoscopic structure of the second material from the third information indicating the thickness of the second material so that the user may easily read the object imaged in the first X-ray image.

Next, in operation S1270, the X-ray image processing method 1200 may generate a final image (for example a final X-ray image generated by post-processing the first X-ray image) on which a post-processing result is reflected. Also, operation S1270 may generate the final second information and the final third information based on the second information and the third information as described above. Operation S1270 may be performed by the image processor 220. The final X-ray image may be an image generated by removing a noise component included in the first X-ray image.

Also, the controller 320 may control the final X-ray image to be displayed on the display 340. Also, the controller 320 may control a user interface screen including the final X-ray image to be displayed on the display 340. Also, the controller 320 may control a user interface screen including at least one of the final X-ray image, the first information, the second information, or the third information to be displayed on the display 340.

Figure 13:
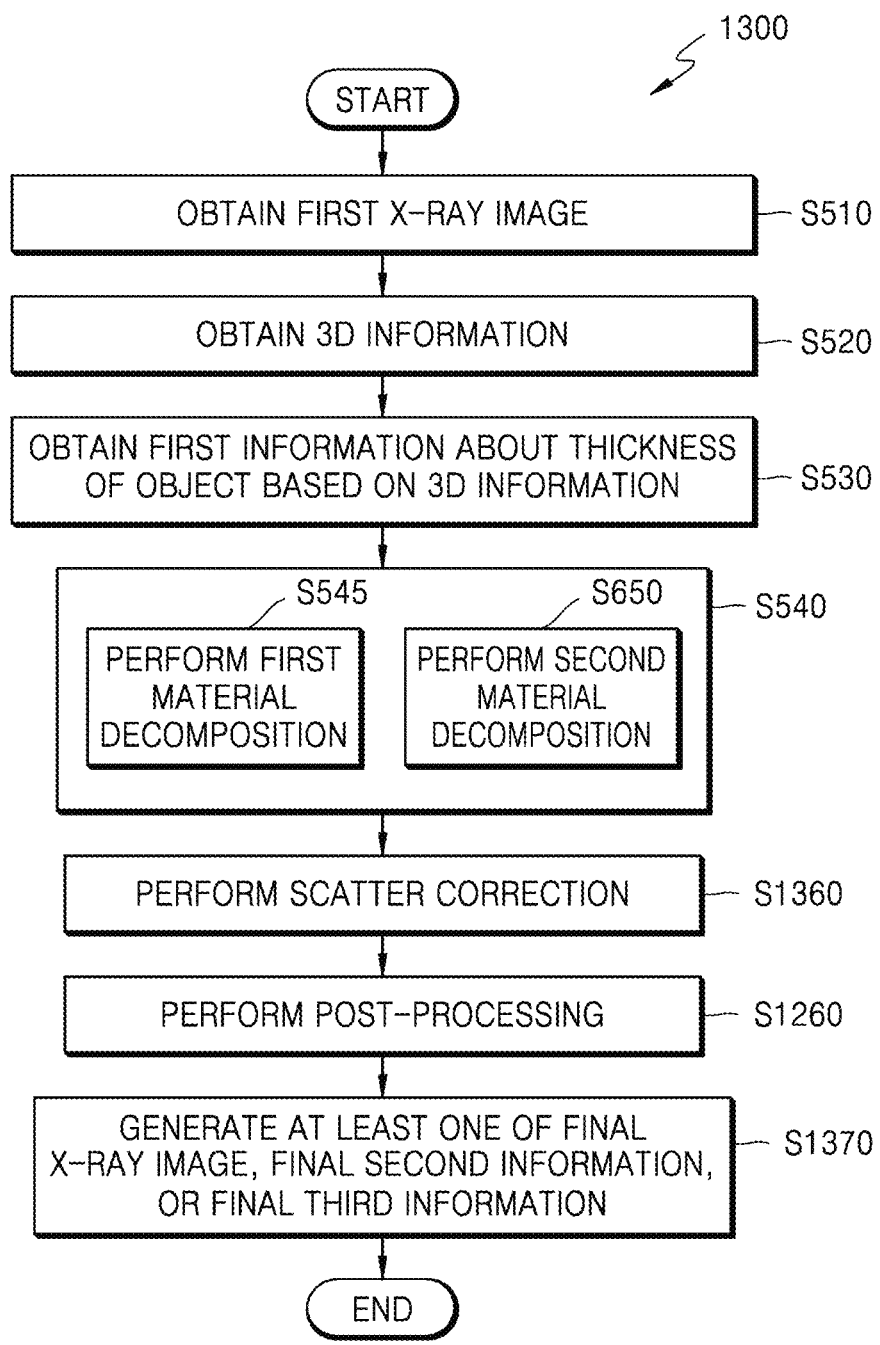
FIG. 13 is a flowchart illustrating an X-ray image processing method according to another embodiment.

FIG. 13 is a flowchart illustrating an X-ray image processing method according to another embodiment. Also, the same elements in an X-ray image processing method 1300 of FIG. 13 as those of the X-ray image processing method 1200 of FIG. 12 are denoted by the same reference numerals. Hence, the same description of the X-ray image processing method 1300 as that made with reference to FIGS. 1 through 12 will be omitted.

The X-ray image processing method 1300 may perform scatter correction as post-processing on the first X-ray image. The term 'scatter correction' may refer to a process of removing or reducing scattering noise caused by a scattered X-ray generated during X-ray imaging. A scatter correction operation may include operations for removing a scatter component in an image including scatter estimation.

When the X-ray emitter 311 emits an X-ray to an object and the X-ray collides with the object, a scattered X-ray is generated. A part of the scattered X-ray is reflected inside and/or outside the object and spreads inside the object and/or in a space where the object is located. The scattered X-ray causes noise in an X-ray image, thereby reducing the quality of the X-ray image. Accordingly, the quality of the first X-ray image may be improved by performing scatter correction.

Also, as described with reference to FIGS. 1 through 12, a thickness of a bone and a thickness of soft tissue may be obtained by using X-ray absorption characteristics. The X-ray absorption characteristics are calculated by using an intensity of an output X-ray and an intensity of an X-ray detected by the X-ray detector 313 (i.e., an intensity of an X-ray transmitted through the object and then detected) as described above. Accordingly, the thickness of the bone and the thickness of the soft tissue may be accurately obtained when the intensity of the X-ray transmitted through the object and then detected is accurately measured. Also, in order to accurately measure the intensity of the X-ray transmitted through the object and then detected, the effect of scattered radiation has to be minimized. Hence, the thickness of the bone and the thickness of the soft tissue may be accurately obtained by performing scatter correction.

Referring to FIG. 13, the X-ray image processing method 1300 may perform operation S1360 that is a scatter correction operation after operation S540. Operation S1360 may be performed by the image processor 220.

In detail, the image processor 220 may perform scatter correction on the first X-ray image based on the second information and the third information, and may update the second information and the third information based on the scatter-corrected first X-ray image.

Once X-ray scattering occurs, a degree of scattering and scattering characteristics of materials included in a human body that is the object are changed. Accordingly, it is difficult to estimate a scattered X-ray without accurately decomposing the materials of the human body.

Accordingly, after the materials of the object are decomposed, the scattered X-ray may be estimated based on the decomposed materials. Hence, the X-ray image processing method 1300 may perform operation S540 in which a plurality of different materials included in the object, for example the first material and the second material, are decomposed, and then may perform operation S1360 in which a scattered X-ray is estimated based on the decomposed first material and second material. In operation S1360, the X-ray image processing method 1300 may perform scatter correction on the first X-ray image based on the estimated scattered X-ray.

Also, in operation S1370, the X-ray image processing method 1100 may obtain at least one of the final X-ray image, the final second information, or the final third information based on the scatter-corrected first X-ray image. Operation S1370 may be performed by the image processor 220.

In detail, the image processor 220 may obtain the scatter-corrected first X-ray image as the final X-ray image. In an embodiment, the image processor 220 may re-obtain the second information and the third information based on the scatter-corrected first X-ray image. The first X-ray image that is scatter-corrected may be referred to as the final X-ray image, and the second information and the third information obtained based on the final X-ray image may be respectively referred to as the final second information and the final third information. Also, the scatter correction may be repeatedly performed at least once.

An example of the scatter correction will be described in detail with reference to FIGS. 14 and 15.

Figure 14:
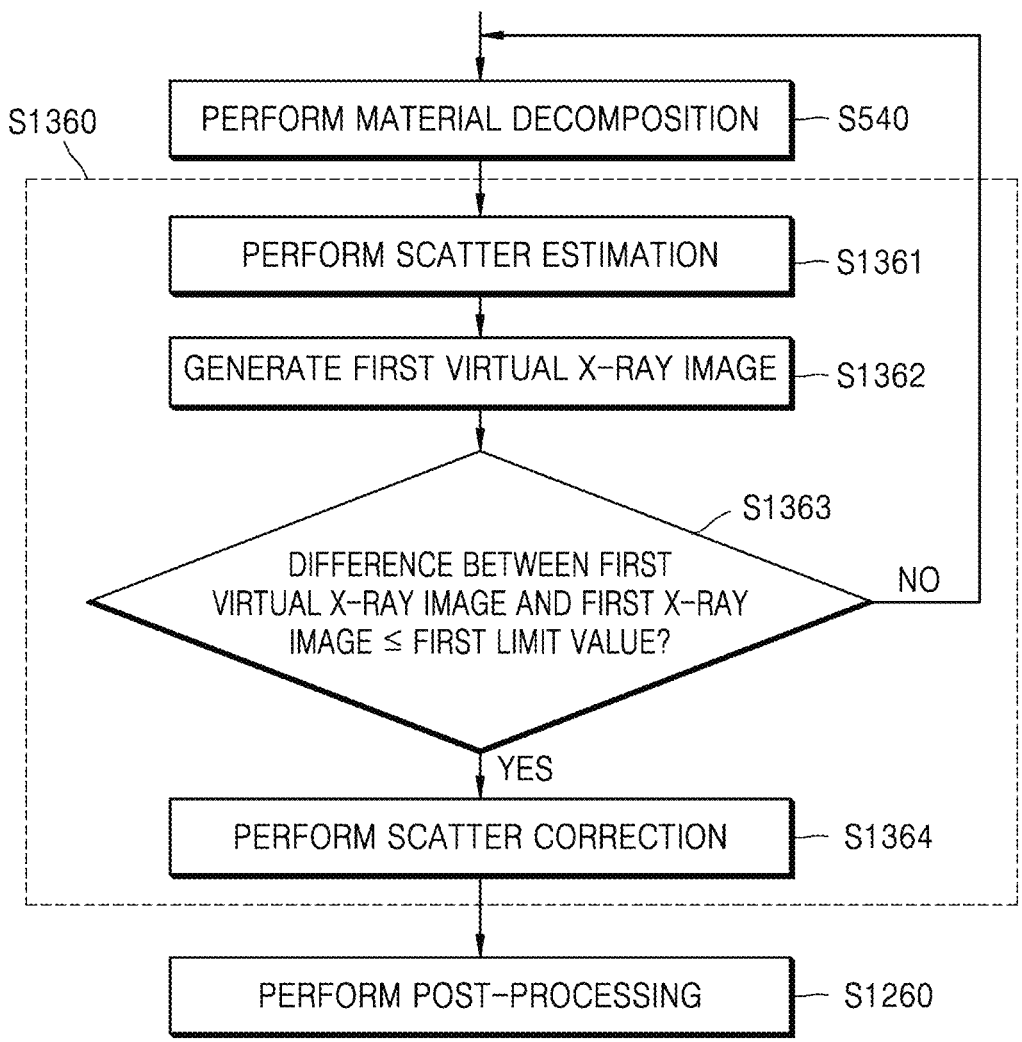
FIG. 14 is a diagram for describing a scatter correction operation according to an embodiment.

FIG. 14 is a diagram for describing a scatter correction operation according to an embodiment.

Figure 15:
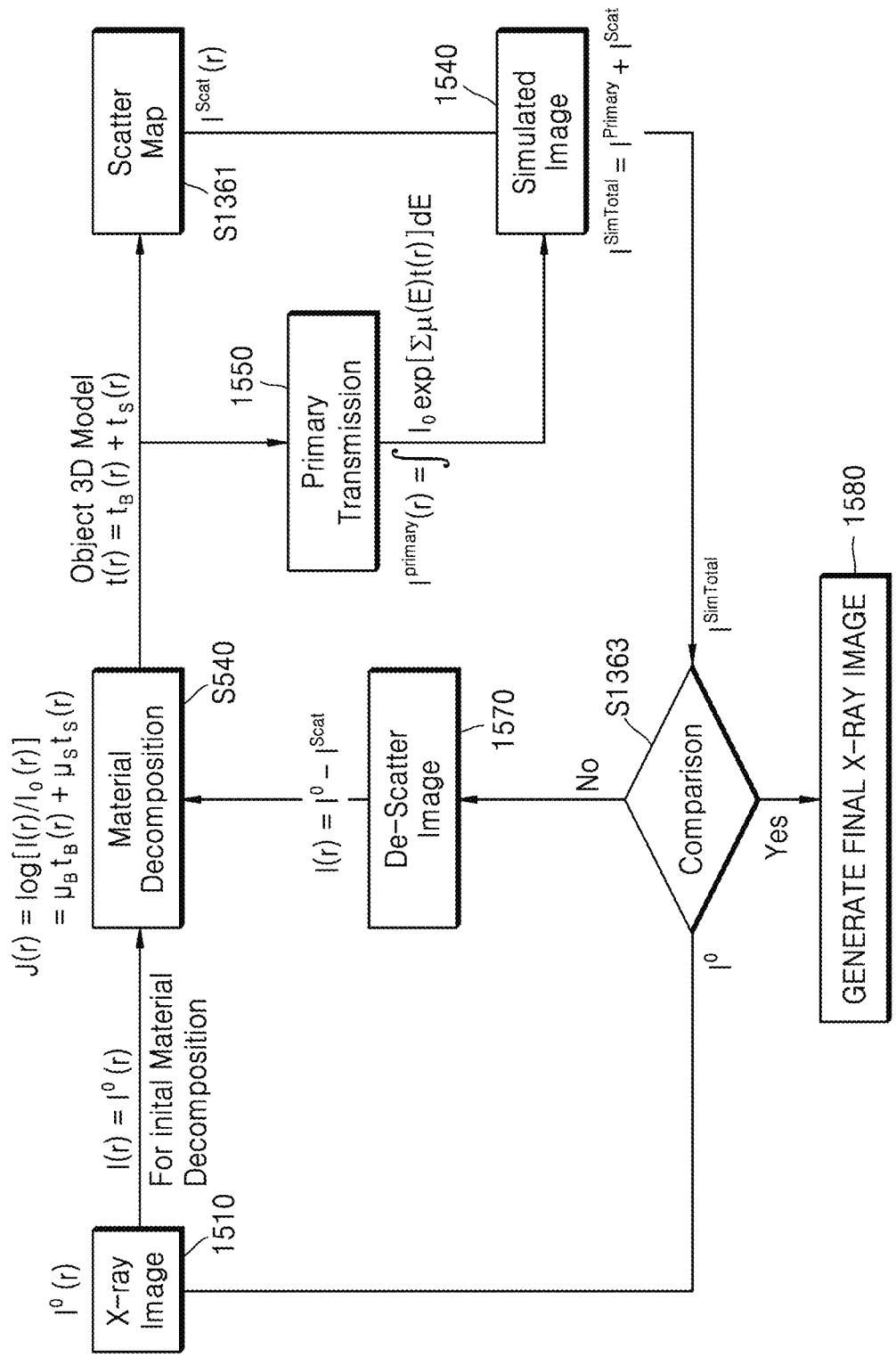
FIG. 15 is a diagram for describing a scatter correction operation according to another embodiment.

FIG. 15 is a diagram for describing a scatter correction operation according to another embodiment.

In operations of FIGS. 14 and 15, the same elements as those of FIG. 13 are denoted by the same reference numerals. Hence, the same description of elements of FIGS. 14 and 15 as that made with reference to FIG. 13 will be omitted.

Referring to FIG. 14, after operation S540 in which material decomposition of decomposing the first material and the second material that are different materials included in the object and obtaining information about the first material and the second material is performed, operation S1361 in which a scattered X-ray is estimated based on information obtained by the material decomposition, e.g., the second information and the third information, may be performed. A process of estimating the scattered X-ray generated during X-ray imaging for obtaining the first X-ray image is referred to as 'scatter estimation'.

Referring to FIG. 15, an X-ray image 1510 indicates a first X-ray image. In FIG. 15, $I^0(r)$ denotes an actual image obtained through X-ray imaging, that is, a first X-ray image before scatter correction. In detail, the X-ray image 1510 may refer to a first X-ray image that is initially obtained, before scatter correction is performed. When scatter correction is firstly performed and then scatter correction is secondly performed, an X-ray image on which the scatter correction is firstly performed may be referred to as the X-ray image 1510. That is, when scatter correction is to be performed, an image input for the scatter correction may be referred to as the X-ray image 1510.

The following description relates to an embodiment in which the X-ray image 1510 is a first X-ray image input for scatter correction.

$I_o$ denotes an intensity of an X-ray emitted to an object (for example an intensity of an X-ray generated by the X-ray emitter 311 and output to the object 312) as in [Equation 1]. $I(r)$ denotes a first X-ray image that is generated by updating. In detail, $I(r)$ denotes an X-ray image that is generated by scatter correction. 'r' may denote a position corresponding to a pixel r (or an $r^{th}$ pixel) in a region of the object to be imaged. That is, $I(r)$ may indicate an intensity of an X-ray detected at the position corresponding to the pixel r (or the $r^{th}$ pixel). In an embodiment, $I(r)$ may correspond to an image value (or a pixel value) of the pixel r (or the $r^{th}$ pixel) of the first X-ray image.

Referring to FIG. 14, operation S1360 that is a scatter correction operation may include operation S1361 in which scattered radiation generated during X-ray imaging for obtaining the first X-ray image is estimated based on the second information and the third information and operations S1362, S1363, and S1364 in which scatter correction is performed based on a result obtained after estimating the scattered radiation.

In detail, operation S1360 may include a step of generating a scatter map corresponding to a scattered X-ray component in the first X-ray image based on the second information and the third information and a step of obtaining the first X-ray image scatter corrected by removing a noise component corresponding to the scattered X-ray in the first X-ray image by using the scatter map.

In detail, operation S1361 that is a scatter estimation operation may include a step of generating a scatter map showing a distribution of a scattered X-ray in the first X-ray image based on the second information and the third information.

Operation S1360 may include operation S1362 in which a first virtual X-ray image showing the object and generated through projection simulation is obtained based on the second information and the third information. In detail, operation S1362 in which the first virtual X-ray image is obtained may include a step of generating a projection image (for example a primary transmission image) by allowing an incident X-ray to pass through a phantom corresponding to the object through projection simulation, a step of generating a scatter map showing a distribution of a scattered X-ray in the first X-ray image based on the second information and the third information, and a step of obtaining the first virtual X-ray image by adding the projection image and the scatter map. An example of operation S1362 will be described in detail with reference to FIGS. 14 and 15.

Next, in operation S1363, whether to update the scatter map obtained in operation S1361 may be determined based on a comparison result between the first virtual X-ray image and the first X-ray image. In operation S1364, scatter correction may be performed based on a determination result of operation S1363.

A scatter correction operation will be described in more detail with reference to FIG. 15.

Referring to FIG. 15, I(r) of FIG. 15 denotes an X-ray image generated by performing scatter correction on a first X-ray image. Before the scatter correction is performed, $I^0(r)$ and I(r) may be the same.

Also, a detailed explanation of the same variables in equations of FIG. 15 as variables in [Equation 1] through [Equation 8] will be omitted.

Referring to FIG. 15, operation S1361 that is a scatter estimation operation may be performed based on second information and third information. In detail, operation S1361 may generate a scatter map corresponding to a scattered X-ray in a first X-ray image, based on the second information and the third information.

Referring to FIG. 15, the X-ray image processing method 1300 may perform operation S1361 to obtain $I^{Scat}(r)$ that is a scatter map.

In detail, a first material (for example soft tissue) is decomposed and a second material (for example a bone) is decomposed from the first X-ray image 1510. A scatter map may be generated by using t(r) that is a thickness distribution of the decomposed materials.

In detail, when a thickness distribution of the first material and a thickness distribution of the second material are known, how X-ray scattering occurs inside and/or outside the object may be estimated according to a density, an attenuation coefficient, a volume, and any other characteristic of each of the first material and the second material. The scatter map indicates a distribution of a scattered X-ray in an X-ray image. In detail, the scatter map may indicate a scattered X-ray generated inside and/or outside the object imaged in the first X-ray image and may be expressed as 2D information. In detail, the scatter map may be expressed as 2D image data having a resolution and an image size corresponding to a resolution and an image size of the first X-ray image.

In operation S1364, scatter correction of removing a noise signal corresponding to the scattered X-ray from the first X-ray image may be performed by using the scatter map. Operation S1364 may be performed by the image processor 220.

In detail, a scatter-corrected first X-ray image may be generated by removing a scattered X-ray component included in the scatter map in the first X-ray image 1510. For example, the scattered X-ray image component may be removed from the first X-ray image 1510 by subtracting the scatter map from the first X-ray image 1510. The scatter-corrected first X-ray image is illustrated as a de-scatter image 1570 and is denoted by I(r). In detail, I(r) that is the scatter-corrected first X-ray image may be defined as in [Equation 9].

$$I(r)=I^0(r)-I^{Scat}(r) \quad \text{[Equation 9]}$$

Also, in operation S1362, the X-ray image processing method 1300 may generate a first virtual X-ray image, and in operations S1363 and S1364, the X-ray image processing method 1300 may perform scatter correction based on a comparison result between the first virtual X-ray image and the first X-ray image. Operations S1363 and S1364 may be performed by the image processor 220. The first virtual X-ray image is a simulated image 1540 generated based on the second information, the third information, and the scatter map.

In detail, referring to FIG. 15, in operation S540, materials included in an object are decomposed by performing material decomposition, and second information and third information indicating a 3D structure of the decomposed materials are obtained. In detail, when the second information and the third information respectively include information about a thickness of a first material and information about a thickness of a second material, a 3D model of the object may be obtained by using the second information and the third information. Also, a phantom corresponding to the 3D model of the object may be generated based on the second information and the third information indicating the 3D structure of the decomposed materials. A transmission image may be generated through a simulation operation of projecting an X-ray to the phantom. The transmission of the X-ray through the phantom corresponding to the 3D model of the object without absorption may be primary transmission 1550. Also, a distribution of the X-ray scattered by the phantom may be represented as a scatter map. In operation S1362, when scattered radiation shown in the scatter map is added to the transmission image, the first virtual X-ray image may be generated. Accordingly, the first virtual X-ray image may be defined as in [Equation 10].

$$I^{SimTotal}(r)=I^{Primary}(r)+I^{Scat}(r) \quad \text{[Equation 10]}$$

In [Equation 10], $I^{SimTotal}(r)$ denotes the first virtual X-ray image, and $I^{Primary}(r)$ denotes the transmission image.

In operation S1363, the image processor 220 may determine whether to update the scatter map based on a comparison result between the first virtual X-ray image and the first X-ray image 1510. Operation S1363 may be performed by the image processor 220.

In detail, in operation S1364, when a difference value between the first virtual X-ray image and the first X-ray image is equal to or less than a first limit value, the image processor 220 may perform post-processing of scatter correcting the first X-ray image, and in operation 1580, the image processor 220 may generate a final X-ray image.

When a difference value between the first virtual X-ray image and the first X-ray image is greater than the first limit value, the image processor 220 may return to operation S540 to update the scatter map, and may update the scatter map by re-performing operation S540 that is a material decomposition operation and operation S1361 that is a scatter estimation operation. When the scatter map is updated, the first X-ray image may be scatter corrected by using the previously obtained scatter map (i.e., the scatter map before updating), the second information and the third information may be re-obtained based on the scatter-corrected first X-ray image, and the scatter map may be re-obtained based on the re-obtained second information and third information. The re-obtained scatter map may be an updated scatter map that is re-obtained based on the re-obtained second information and third information. That is, as in [Equation 9], the scatter-corrected first X-ray image may be generated by subtracting a signal component in the scatter map from the first X-ray image. The scatter map may be updated by re-performing operation S540 that is a material decomposition operation and operation S1361 that is a scatter estimation operation based on the scatter-corrected first X-ray image.

In detail, the first limit value may be a reference value for comparing a similarity between the first X-ray image and the first virtual X-ray image. In detail, when a difference between the first X-ray image and the first virtual X-ray image and the first limit value are compared with each other, a value that allows the difference between the first X-ray image and the first virtual X-ray image to be within a set error range may be determined as the first limit value. The difference between the first X-ray image and the first virtual X-ray image may be expressed as a mean square value or the like. Also, the set error range may be set by the X-ray apparatus 100, the X-ray image processing apparatus 200, 300, or 400, or a user in consideration of target image quality of the first X-ray image.

In an embodiment, scatter correction may be repeatedly performed. In detail, a scatter correction operation may be repeatedly performed until a difference value between the first virtual X-ray image and the first X-ray image in operation S1363 is equal to or less than the first limit value.

In detail, operation S540 that is a material decomposition operation and operation S1361 that is a scatter estimation operation may be repeatedly performed until the scatter-corrected X-ray image is within an error range in operation S1363 that is a comparison operation of FIGS. 14 and 15, thereby generating a final X-ray image having the best image quality. Accordingly, the second information and the third information are obtained based on the final X-ray image. Accordingly, the accuracy of the second information and the third information may be improved.

Figure 16:
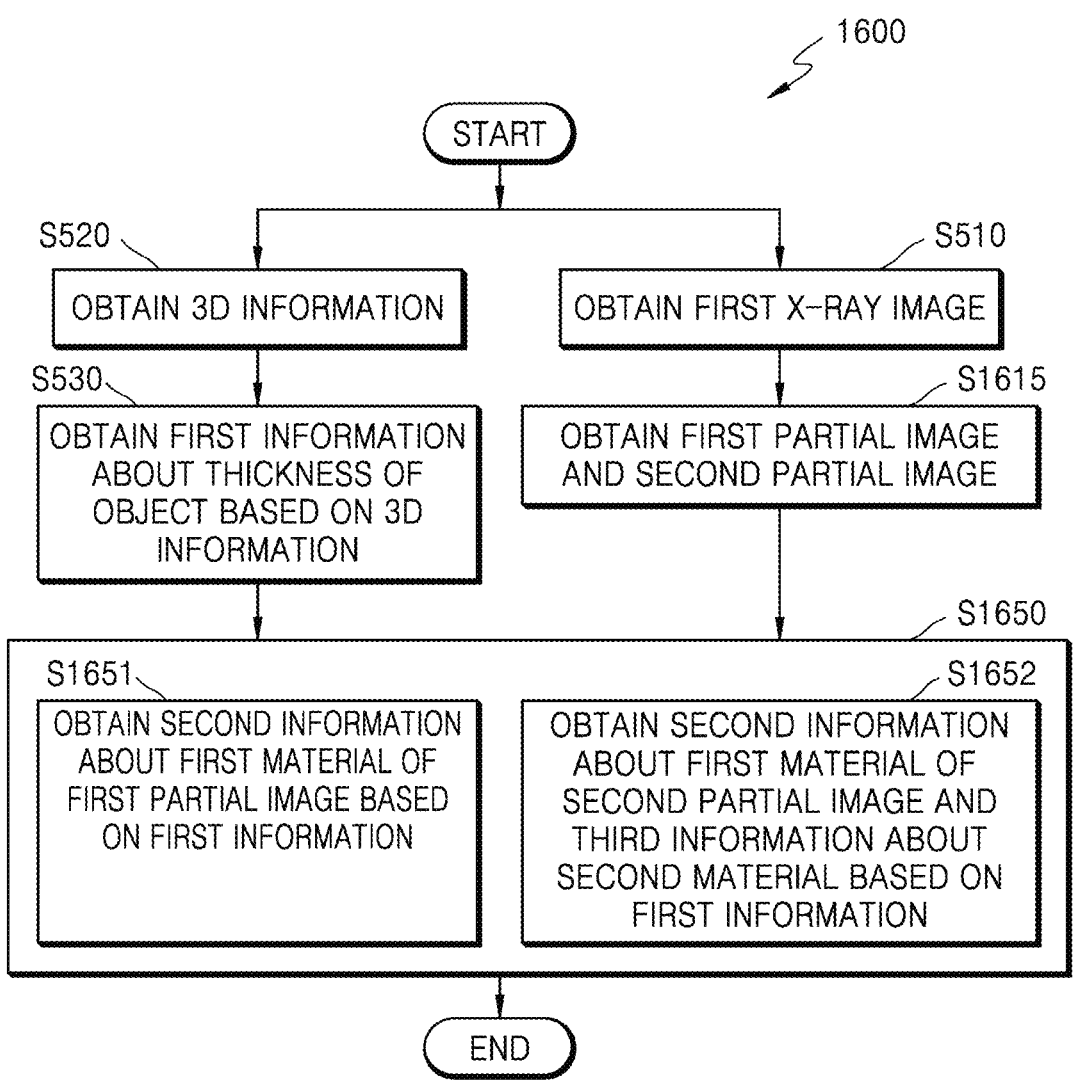
FIG. 16 is a flowchart illustrating an X-ray image processing method according to another embodiment.

FIG. 16 is a flowchart illustrating an X-ray image processing method according to another embodiment. An X-ray image processing method 1600 of FIG. 16 may be performed by the X-ray image processing apparatus 200, 300, or 400 according to an embodiment described with reference to FIGS. 2 through 4. Accordingly, each operation of the X-ray image processing method 1600 may be performed by each element of the X-ray image processing apparatus 200, 300, or 400. Also, the same elements in the X-ray image processing method 1600 as those of the X-ray image processing method 500, 600, or 700 of FIGS. 5 through 7 are denoted by the same reference numerals. Hence, the same description of the X-ray image processing method 1600 as that made with reference to FIGS. 1 through 15 will be omitted.

Referring to FIG. 16, in operation S1615, the X-ray image processing method 1600 may obtain a first partial image generated by imaging the first material and a second partial image generated by imaging the first material and the second material in an overlapping manner from the first X-ray image obtained in operation S510. Operation S1615 may be performed by the image processor 220.

In operation S1650, second information corresponding to the first material and third information corresponding to the second material may be obtained based on the first partial image and the second partial image and the first information obtained based on the 3D information. Operation S1650 may be performed by the image processor 220. In detail, in operation S1651, the second information related to a stereoscopic structure of the first material may be obtained based on the first information and the first partial image, and in operation S1652, the third information related to a stereoscopic structure of the second material may be obtained based on the first information and the second partial image.

In detail, the first partial image is a region where only the first material is imaged in the first X-ray image. The second partial image is a region where the first material and the second material are imaged in an overlapping manner in the first X-ray image.

An example of operations of the X-ray image processing method 1600 will be described in detail with reference to the X-ray image processing apparatus 300 of FIG. 3 and FIGS. 17 through 19.

The image processor 220 may segment a region where only the first material in the first X-ray image is imaged as the first partial image, and may segment a region where the first material and the second material in the first X-ray image are imaged in an overlapping manner as the second partial image.

In detail, segmentation or extraction of the first partial image and the second partial image may be performed based on intensity values of an X-ray transmitted through the object. In detail, segmentation or extraction of the first partial image and the second partial image may be performed based on intensity values of an X-ray detected by, for example, the X-ray detector 313 to capture the first X-ray image. In an embodiment, segmentation or extraction of the first partial image and the second partial image may be performed based on pixel values of the first X-ray image.

For example, the image processor 220 may extract a region imaged with pixel values corresponding to intensity values of an X-ray transmitted through the first material in the first X-ray image as the first partial image. Also, the image processor 220 may obtain the second partial image adjacent to the first partial image and corresponding to a boundary between a region where the first material exists and a region where the first material and the second material exist in an overlapping manner. In detail, the first partial image and the second partial image may be images adjacent to each other at a boundary between the first material and the second material. That is, the first partial image includes a region where only the first material is imaged at the boundary between the first material and the second material. The second partial image includes a region where the first material and the second material are imaged in an overlapping manner at the boundary between the first material and the second material.

In detail, the image processor 220 may obtain the second information about the first material from the first partial image by using the first information about a thickness of the object. Also, the image processor 220 may obtain the third information from the second partial image by using X-ray absorption characteristics, the first information, and the second information. The X-ray absorption characteristics refer to characteristics in which at least a part of an X-ray output (or emitted) to the object is absorbed by a material in the object, and only at least a part of the output X-ray passes through the object and is detected. Because the output X-ray is attenuated while passing through the object, the X-ray absorption characteristics may be referred to as X-ray attenuation characteristics.

Figure 17:
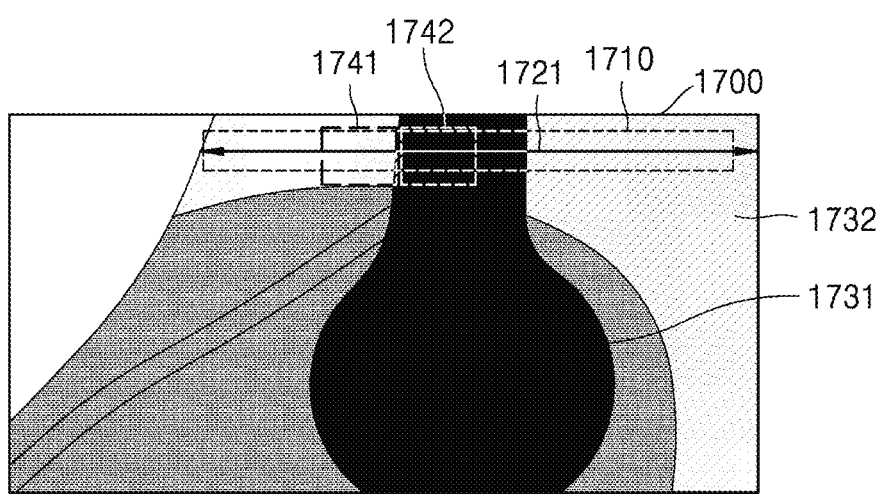
FIG. 17 is a view for describing an operation of obtaining a first partial region and a second partial region according to another embodiment.

FIG. 17 is a view for describing an operation of obtaining a first partial region and a second partial region according to another embodiment.

Referring to FIG. 17, an X-ray image 1700 obtained by imaging a patient's shoulder in order to diagnose a musculoskeletal disorder of the patient is illustrated. In the X-ray image 1700 that is a raw X-ray image, a bone 1731 is the darkest, and soft tissue 1732 adjacent to the bone 1731 and surrounding the bone 1731 is brighter than the bone 1731. Also, an area where X-rays do not penetrate the object may be imaged in white in the X-ray image 1700.

In operation S1615, the image processor 220 obtains the first partial image (for example a region 1741) generated by imaging only the soft tissue 1732 in the first X-ray image (for example the X-ray image 1700) and the second partial image (for example a region 1742) generated by imaging the soft tissue 1732 and the bone 1731 in an overlapping manner. The first partial image includes the region 1741 generated by imaging only the first material at a boundary between the soft tissue 1732 that is the first material and the bone 1731 that is the second material. The second partial image includes the region 1742 generated by imaging the soft tissue 1732 that is the first material and the bone 1731 that is the second material in an overlapping manner at the boundary between the soft tissue 1732 that is the first material and the bone 1731 that is the second material. Because the bone 1731 is surrounded by the soft tissue 1732 such as skin or muscles, a region where the bone 1731 is imaged may be referred to as a region where the bone 1731 and the soft tissue 1732 are imaged in an overlapping manner.

In detail, the image processor 220 may segment or extract a region (for example the region 1741) generated with only pixel values corresponding to the soft tissue from the first X-ray image as the first partial image, based on pixel values of the first X-ray image. In an embodiment, the image processor 220 may segment or extract a region (for example the region 1741) generated with only pixel values corresponding to the soft tissue from the first X-ray image as the first partial image, based on intensity values of an X-ray detected by the X-ray detector 313 of FIG. 3 to capture the first X-ray image. The image processor 220 may segment or extract a region (for example the region 1742) that is adjacent to the first partial image and where the bone and the soft tissue are imaged in an overlapping manner as the second partial image. In detail, the first partial image and the second partial image may indicate regions adjacent to each other at the boundary between the bone and the soft tissue in the first X-ray image.

Also, the first partial image and the second partial image may be obtained through a computation through a neural network. An example of a process of obtaining the first partial image and the second partial image through a neural network computation will be described in detail with reference to FIG. 19.

Figure 19:
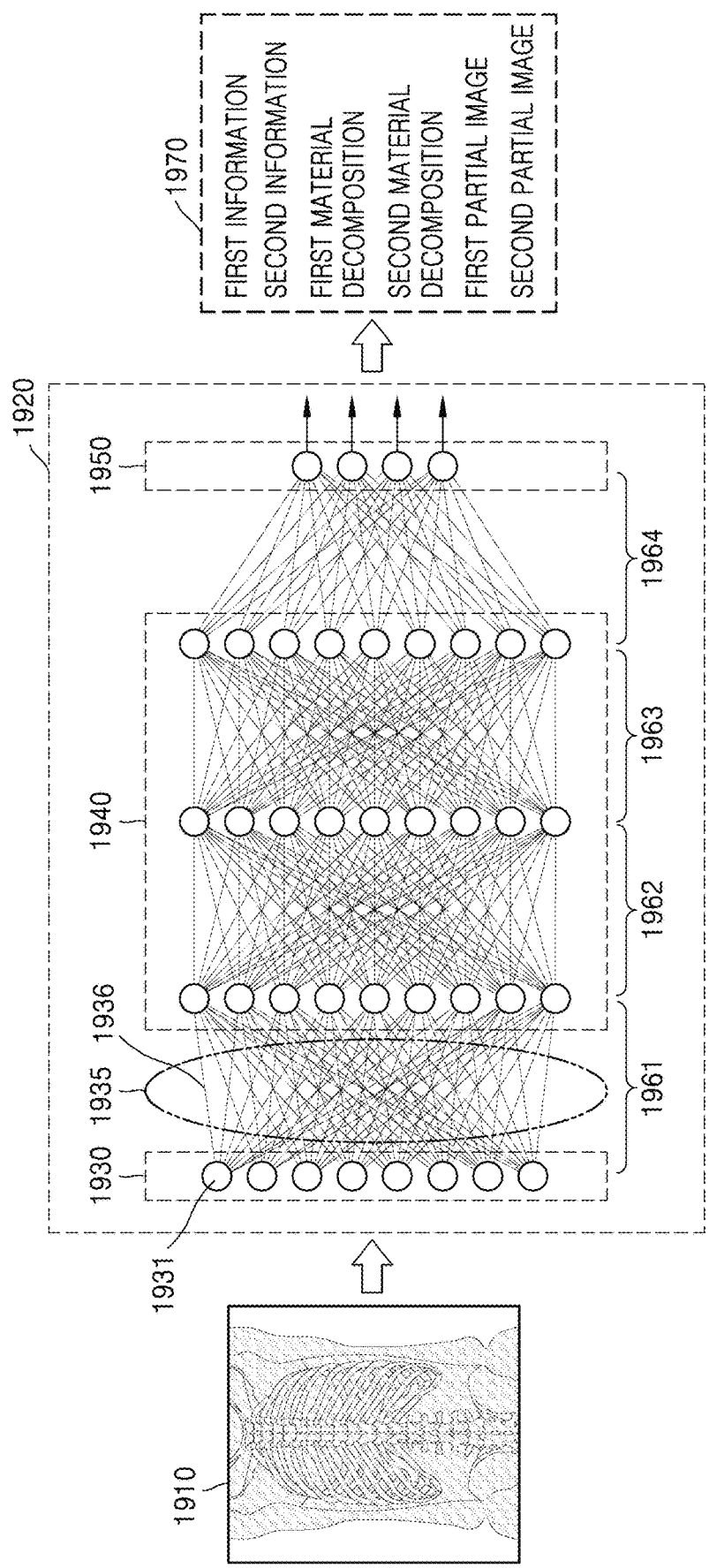
FIG. 19 is a view for describing a neural network through which a computation for obtaining a first partial region and a second partial region is performed.

FIG. 19 is a view for describing a neural network through which a computation for obtaining a first partial region and a second partial region is performed.

The image processor 220 may perform a computation through a neural network, e.g., a DNN 1920, including an input layer, a hidden layer, and an output layer. In FIG. 19, a DNN including hidden layers that are formed at multiple levels is illustrated.

Referring to FIG. 19, the DNN 1920 includes an input layer 1930, a hidden layer 1940, and an output layer 1950. In FIG. 19, the DNN 1920 through which a computation is performed to analyze information included in a first X-ray image that is input data and to segment or extract a first partial image generated by imaging a first material and a second partial image generated by imaging the first material and a second material in an overlapping manner from the first X-ray image is illustrated. In detail, when input data is a first X-ray image 1910, the DNN 1920 may analyze an object to be imaged and included in the first X-ray image 1910, may extract the first partial image generated by imaging the first material and the second partial image generated by imaging the first material and the second material in an overlapping manner, and may output an extraction result as output data 1970.

The first X-ray image 1910 input to the input layer 1930 corresponds to a first X-ray image obtained in operation S510.

A plurality of layers included in the DNN 1920 may include a plurality of nodes (for example 1931) that receive data. Two adjacent layers are connected to each other through a plurality of edges (for example 1936). Each of the nodes has a corresponding weight value, and thus the DNN 1920 may obtain output data based on a value obtained by performing a computation, for example a convolution operation, on an input signal and a weight value.

The DNN 1920 may perform inference and estimation based on a neural network, and a DNN computation may include a CNN computation. That is, the DNN 1920 according to an embodiment may be implemented as a CNN that performs a CNN computation.

Referring to FIG. 19, the input layer 1930 receives the first X-ray image 1910 obtained by imaging the chest that is the object.

In FIG. 19, the hidden layer 1940 includes three-level layers. A depth of the hidden layer 1940 may vary according to order specifications and/or design specifications of a used neural network.

Referring to FIG. 19, the DNN 1920 may include a first layer 1961 formed between the input layer 1930 and a first hidden layer, a second layer 1962 formed between the first hidden layer and a second hidden layer, a third layer 1963 formed between the second hidden layer and a third hidden layer, and a fourth layer 1964 formed between the third hidden layer and the output layer 1950.

The plurality of nodes included in the input layer 1930 of the DNN 1920 receive a plurality of data corresponding to the first X-ray image 1910. The plurality of data may be a plurality of partial images generated by performing filter processing to segment the first X-ray image 1910.

Through a computation on a plurality of layers included in the hidden layer 1940, the output layer 1950 may output the output data 1970 obtained as a result of analyzing the first X-ray image 1910. The output data 1970 may include the first partial image generated by imaging the first material and the second partial image generated by imaging the first material and the second material in an overlapping manner.

In detail, when the DNN 1920 is implemented as a CNN and correlation among pieces of information included in an image is local, the CNN may introduce a filter applied only to a specific area, may perform convolution on pieces of information in the filter, and may precisely extract information about the feature of the image in the filter.

In detail, in the hidden layer 1940 existing in the DNN 1920 based on the CNN, a convolution layer and a pooling layer are alternately located and a depth of each layer filter increases from left to right. Also, a final end of the DNN 1920 based on the CNN may be implemented as a fully connected layer. The convolution layer is a layer of data generated according to a convolution operation, and the pooling layer is a layer for reducing the number or a size of data through an operation such as sub-sampling or pooling. Data (for example a feature map) indicating characteristics of an input image is generated while passing through the convolution layer and the pooling layer. In detail, through a computation through the hidden layer 1940, image features of the first X-ray image 1910 may be generated, and the first partial image generated by imaging only the first material and the second partial image generated by imaging the first material and the second material in an overlapping manner may be more precisely extracted based on the image features.

When the data generated by passing through the convolution layer and the pooling layer is processed through a hidden layer implemented as a fully connected layer, the first partial image and the second partial image to be extracted or segmented may be extracted and output.

Also, in order to improve the accuracy of data output through the DNN 1920, training may be performed in a direction from the output layer 1950 to the input layer 1930 and weight values of the nodes (for example 1931) included in the DNN 1920 may be corrected to improve the precision of the output data. Accordingly, before the first X-ray image 1910 is input, a plurality of different X-ray images may be used in the training of the DNN 1920 and the DNN 1920 may correct a weight value of each node in a direction in which the first partial image generated by imaging the first material included in the X-ray image and the second partial image generated by imaging the first material and the second material are accurately detected.

Also, the DNN 1920 may perform a computation for obtaining first information about a stereoscopic structure of the first material and second information about the second material based on the first partial image and the second partial image.

Also, the DNN 1920 may perform a computation for first material decomposition and second material decomposition based on the first information and the second information. The DNN 1920 may output a result of the computation through the output layer 1950.

Next, in operation S1650, the X-ray image processing method 1600 obtains second information related to a stereoscopic structure of the first material based on the first partial image (for example the region 1741) included in the first X-ray image (for example the X-ray image 1700). Operation S1650 may be performed by the image processor 220. In operation S1650, the X-ray image processing method obtains the second information about the first material and third information about the second material in the second partial image based on the first information and the second partial image (for example the region 1742) obtained in operation S1650. Operation S1650 may be performed by the image processor 220.

Referring to FIGS. 8 and 17, the bone 812 and the soft tissue 811 of FIG. 8 may respectively correspond to the bone 1731 and the soft tissue 1732 of FIG. 17. Also, a first partial region where only tissue is imaged may correspond to the region 821 (1) and a second partial region where soft tissue and a bone are imaged in an overlapping manner may correspond to the region 822 (2).

In the first partial image generated by imaging only the soft tissue that is the first material, a thickness $t_S$ of the soft tissue may be represented as PT that is a thickness of the first information. That is, $t_S$=PT. In the second partial image generated by imaging the soft tissue that is the first material and the bone that is the second material in an overlapping manner, [Equation 2] is represented as [Equation 6].

Hence, in operation S1651, the thickness $t_S$ of the soft tissue in the first partial image may be obtained by using the first information (for example, the first information obtained in operation S530) about a thickness of the object corresponding to the first partial image (for example the region 1741 or the region 821 (1) of FIG. 8) generated by imaging only the soft tissue.

Because the thickness $t_S$ (=PT), a density, and an attenuation coefficient of the soft tissue are known and $I_o$ is known, to that is a thickness of the bone may be obtained by using [Equation 6] indicating X-ray absorption characteristics. I in [Equation 6] may be an intensity value of an X-ray that is transmitted through a portion of the object 810 where the bone and the soft tissue overlap and is detected. Accordingly, I may have a measured value, and the measured value may be applied to [Equation 6].

When the first partial image and the second partial image are adjacent at a boundary (for example the boundary 832) between the bone and the soft tissue, a thickness of the soft tissue imaged in the second partial image may be obtained based on the first information about a thickness of the object.

Figure 18:
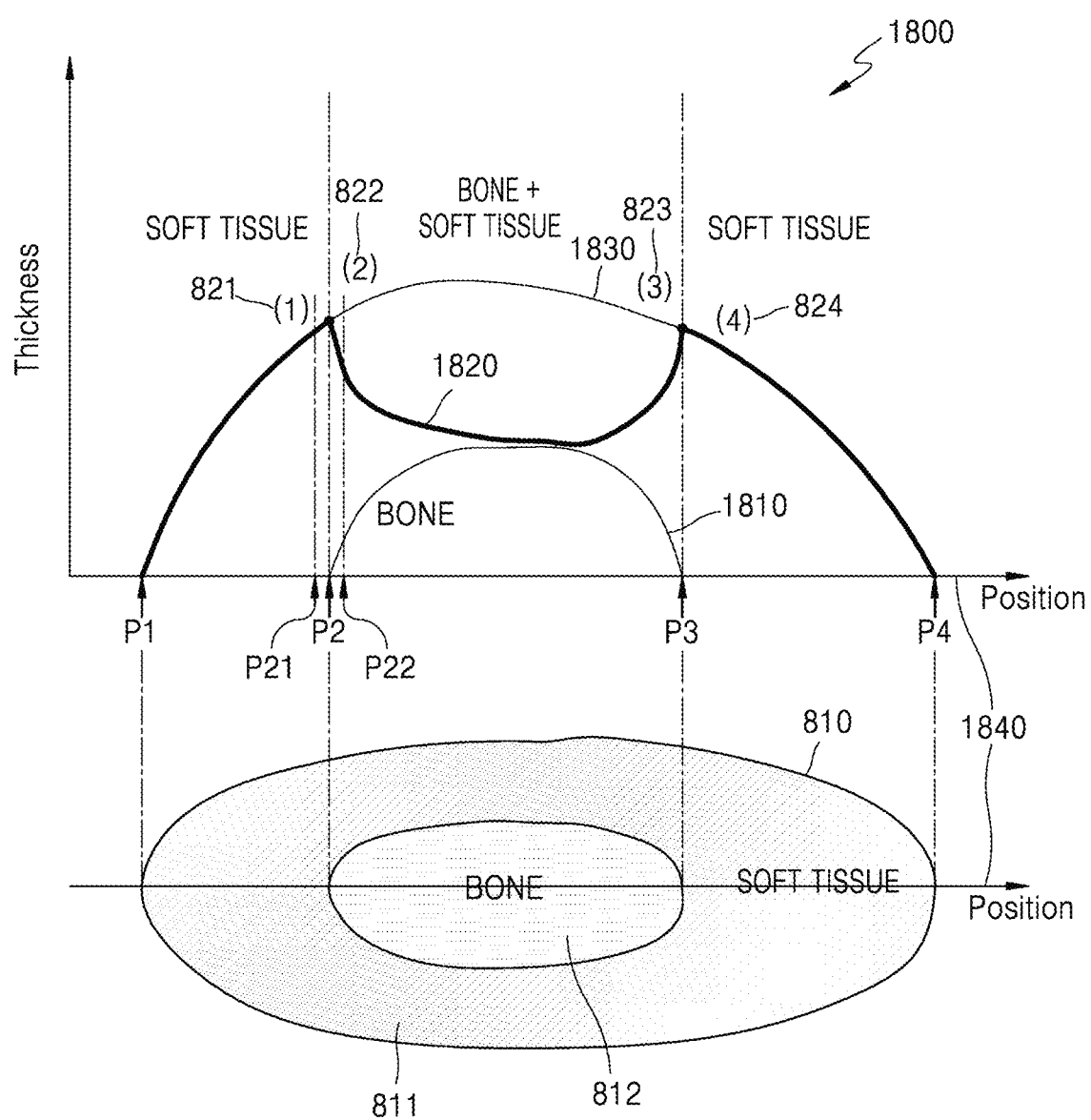
FIG. 18 is a view for describing an operation of obtaining a thickness of a bone and a thickness of soft tissue according to another embodiment.

FIG. 18 is a view for describing an operation of obtaining a thickness of a bone and a thickness of soft tissue according to another embodiment.

FIG. 18 is a view for describing thicknesses of materials in an object imaged in an X-ray image. In FIG. 18, the same elements as those of FIG. 8 are denoted by the same reference numerals. Graphs 1800 of FIG. 18 are graphs for describing a thickness of an object in a vertical cross-section of the object along a predetermined axis (for example a perpendicular line 1721 of FIG. 17). The X-axis 1840 of FIG. 18 may correspond to the X-axis of the graph 850 of FIG. 8. The Y-axis of the graphs 1800 of FIG. 18 represents thicknesses of materials included in the object 810.

Referring to FIG. 18, a graph 1820 shows a thickness of soft tissue, and a graph 1810 shows a thickness of a bone. The graph 1830 shows a thickness of the object 810 including the bone and the soft tissue.

Referring to FIGS. 18 and 8, in the object 810, only the soft tissue exists in the interval between the position P1 corresponding to the boundary 831 of the object 810 and the position P2 corresponding to the boundary 832 between the soft tissue and the bone, and a thickness of the soft tissue in the interval between the positions P1 and P2 gradually increases. A thickness of the soft tissue in the interval between the positions P1 and P2 may be obtained by using X-ray absorption characteristics, specifically, [Equation 11].

$$J = -\log\left[\frac{I}{Io}\right] = \mu_S \rho_S t_S \quad \text{[Equation 11]}$$

Next, a thickness of the bone 812 may start to increase as shown in the graph 1810 from the boundary 832 between the soft tissue 811 and the bone 812.

Thicknesses of the object 810 at two adjacent positions P21 and P22 based on the boundary 832 between the soft tissue 811 and the bone 812 may have the same value or similar values. In detail, because a thickness distribution of the object 810 is continuous, a thickness distribution of the object 810 at the boundary 832 between the soft tissue 811 and the bone 812 is continuous. That is, a thickness of the object 810 does not start to sharply change but starts to smoothly change from the boundary 832 between the soft tissue 811 and the bone 812. As such, total thickness distribution characteristics of materials included in a human body may be represented as shown in the graph 1830 of FIG. 18. The total thickness distribution characteristics of the materials included in the human body may be referred to as a smooth thickness shift principle.

Also, the total thickness distribution characteristics may have a known shape obtained based on a diagnosis result of a plurality of patients. That is, the graph 1830 of FIG. 18 may have a shape that is experimentally or statistically known. Also, the graph 1830 of FIG. 18 may be modeled through a human body model or a human body profile based on a thickness distribution measurement result of the plurality of patients.

Accordingly, when a thickness of the soft tissue 811 at the position P2 or P21 corresponding to the boundary 832 between the soft tissue 811 and the bone 812 is known, a thickness of the soft tissue 811 imaged in the second partial region adjacent to the boundary 832 between the soft tissue 811 and the bone 812 may be known. Because the position P21 and the position P22 are adjacent to each other based on the position P2 corresponding to the boundary 832 between the soft tissue 811 and the bone 812, a total thickness of the object 810 at the position P21 and a total thickness of the object 810 at the position P22 continuously smoothly change.

Because a thickness of the object 810 is continuous as shown in the graph 1830, it may be assumed that a total thickness of the object 810 measured at the position P21 is the same as a total thickness of the object 810 measured at the position P22.

Accordingly, [Equation 12] may be obtained.

$$t_{s1} = t_{s2} + t_{B2} \quad \text{[Equation 12]}$$

In [Equation 12], s1 denotes the soft tissue 811 existing in an object region imaged in the first partial image, s2 denotes the soft tissue 811 existing an object region imaged in the second partial image, and B2 denotes the bone 812 existing in an object region imaged in the second partial image. That is, $t_{S1}$ denotes a thickness of the soft tissue 811 imaged in the first partial image, $t_{S2}$ denotes a thickness of the soft tissue 811 imaged in the second partial image, and $t_{B2}$ denotes a thickness of the bone 812 imaged in the second partial image. Also, $t_{s1}$ denotes a thickness of the soft tissue 811 at the position P21 (position in the object 810 corresponding to the first partial image) adjacent to the boundary 832 between the soft tissue 811 and the bone 812, to denotes a thickness of the soft tissue 811 at the position P22 (position in the object 810 corresponding to the second partial image) adjacent to the boundary 832 between the soft tissue 811 and the bone 812, and $t_{B2}$ denotes a thickness of the bone 812 at the position P22 (position in the object 810 corresponding to the second partial image) adjacent to the boundary 832 between the soft tissue 811 and the bone 812.

As described above, when it is assumed that a total thickness of the object 810 measured at the position P21 is the same as a total thickness of the object 810 measured at the position P22, the thickness $t_{st}$ of the soft tissue 811 that is a total thickness of the object 810 at the position P21 may be the same as a value obtained by summing the thickness $t_{s2}$ of the soft tissue 811 and the thickness $t_{B2}$ of the bone 812 measured at the position P22.

Also, [Equation 12] may be modified to [Equation 13].

$$t_{s2} = t_{s1} - t_{B2} \quad \text{[Equation 13]}$$

Also, in an object region corresponding to the second partial image where the soft tissue and the bone coexist, [Equation 6] may be represented as [Equation 14].

$$J = -\log\left[\frac{I}{Io}\right] = \mu_S \rho_S t_{S2} + \mu_B \rho_B t_{B2} \quad \text{[Equation 14]}$$

In [Equation 14], an attenuation coefficient $\mu_S$ of the soft tissue, a density $\rho_S$ of the soft tissue, an attenuation coefficient $\mu_B$ of the bone, and a density $\rho_B$ of the bone may be known values. I in [Equation 14] is an intensity value of an X-ray that is transmitted through the object where the bone and the soft tissue coexist and is detected, and thus may be measured during X-ray imaging.

When [Equation 13] is applied to $t_{s2}$ in [Equation 14], [Equation 9] may be obtained.

$$J = -\log\left[\frac{I}{Io}\right] = \mu_S \rho_S (t_{S1} - t_{B2}) + \mu_B \rho_B t_{B2} \quad \text{[Equation 15]}$$

[Equation 15] may be modified to [Equation 16].

$$J = -\log\left[\frac{I}{Io}\right] = (\mu_B \rho_B - \mu_S \rho_S) t_{B2} + \mu_S \rho_S t_{S1} \quad \text{[Equation 16]}$$

In [Equation 16], an attenuation coefficient $\mu_S$ of the soft tissue, a density $\rho_S$ of the soft tissue, an attenuation coefficient $\mu_B$ of the bone, and a density $\rho_B$ of the bone are known values, and $t_{s1}$ is a value obtained by using [Equation 11] indicating X-ray absorption characteristics and the first partial image. I in [Equation 16] is an intensity value of an X-ray that is transmitted through the object where the bone and the soft tissue coexist and is detected, and thus may be measured during X-ray imaging. Hence, in [Equation 16], because all values except the thickness $t_{B2}$ of the bone in an object region corresponding to the second partial image may be assignable values, the thickness $t_{B2}$ may be obtained.

Once the thickness $t_{B2}$ is obtained, the thickness $t_{s2}$ of the soft tissue in an object region (for example, an object region corresponding to the second partial image) where the bone and the soft tissue coexist may be obtained by applying the thickness $t_{B2}$ and the thickness $t_{s1}$ that is already obtained to [Equation 13].

As described above, in an embodiment, the image processor 220 may obtain both a thickness of the bone and a thickness of the soft tissue in the second partial image.

By using the above method of FIGS. 16 through 18, in an entire region of the object in the X-ray image, thicknesses of the soft tissue and the bone may be measured. According to an embodiment, information about a 3D distribution of the soft tissue and the bone included in the object may be obtained based on the thicknesses of the soft tissue and the bone. Also, according to an embodiment, volumes of the soft tissue and the bone may be obtained based on the thicknesses of the soft tissue and the bone.

FIG. 20 is a flowchart illustrating an X-ray image processing method according to another embodiment. An X-ray image processing method 2000 according to an embodiment may be performed by the X-ray image processing apparatus 200, 300, or 400 according to an embodiment described with reference to FIGS. 2 through 4. Accordingly, each operation of the X-ray image processing method 2000 may be performed by each element of the X-ray image processing apparatus 200, 300, or 400. Also, the same elements in the X-ray image processing method 2000 as those of the X-ray image processing method 500, 600, 700, 1300, or 1600 described with reference to FIGS. 5 through 19 are denoted by the same reference numerals. Hence, the same description of the X-ray image processing method 2000 as that made with reference to FIGS. 1 through 19 will be omitted.

Referring to FIG. 20, in operation S1360, scatter correction may be performed on a first X-ray image based on second information and third information and a scatter-corrected first X-ray image may be generated.

In operation S1615, the X-ray image processing method 2000 obtains a first partial image and a second partial image in the scatter-corrected first X-ray image obtained in operation S1360.

In operation S2030, a first material and a second material may be decomposed from an object based on the first partial image and the second partial image obtained in operation S1615. Operation S2030 may be performed by the image processor 220. Operation S2030 corresponds to material decomposition of FIGS. 16 through 19, specifically, an operation of obtaining second information related to a stereoscopic structure of the first material and obtaining third information related to a stereoscopic structure of the second material by using the first partial image and the second partial image included in the first X-ray image. Accordingly, a detailed explanation will be omitted. Also, operation S2030 may include an operation of updating the second information and the third information obtained in operations S540 and S1650, and an operation of performing material decomposition based on final second information and final third information obtained after updating.

As described above, the X-ray image processing method 2000 performs scatter correction on the first X-ray image by using 3D information obtained by a 3D camera and then performs material decomposition by using the scatter-corrected first X-ray image. Accordingly, a reduction in the accuracy in the material decomposition due to a noise component corresponding to scattered radiation may be minimized. Accordingly, information related to a stereoscopic structure of each of the first material and the second material may be accurately obtained from the object.

An X-ray image processing method according to embodiments may be implemented as program commands executable through various computer means and may be recorded on a computer-readable recording medium. Also, an embodiment may be implemented as a computer-readable recording medium on which one or more programs including instructions for executing an X-ray image processing method are recorded.

The computer-readable recording medium may include program commands, data files, data structures, and the like separately or in combinations. The program commands to be recorded on the computer-readable recording medium may be specially designed and configured for embodiments or may be well-known to and be usable by one of ordinary skill in the art of computer software. Examples of the computer-readable recording medium include a magnetic medium such as a hard disk, a floppy disk, or a magnetic tape, an optical medium such as a compact disk read-only memory (CD-ROM) or a digital versatile disk (DVD), a magneto-optical medium such as a floptical disk, and a hardware device specially configured to store and execute program commands such as a ROM, a RAM, or a flash memory. Examples of the program commands include advanced language codes that may be executed by a computer by using an interpreter or the like as well as machine language codes that are made by a compiler.

An X-ray image processing method according to embodiments may be implemented as a computer program product including a recording medium storing a program for performing: an operation of obtaining a sentence composed of multiple languages; and an operation of obtaining vector values respectively corresponding to words included in the sentence composed of the multiple languages by using a multilingual translation model, converting the obtained vector values into vector values corresponding to a target language, and obtaining a sentence composed of the target language based on the converted vector values.

An objective of an embodiment is to provide an X-ray image processing method which may obtain information about two or more different materials included in an object by using 3D information obtained by using a 3D camera and one X-ray image and an X-ray image processing apparatus using the X-ray image processing method.

In detail, an objective of an embodiment is to provide an X-ray image processing method which may rapidly obtain information about soft tissue and a bone by using a first X-ray image obtained by emitting an X-ray having a single energy band to an object and 3D information obtained by using a 3D camera and an X-ray image processing apparatus using the X-ray image processing method.

Also, according to an embodiment may obtain information about two or more different materials based on 3D information obtained by using a 3D camera and may remove a noise signal corresponding to scattered radiation in an X-ray image based on the obtained information. Accordingly, the quality of the X-ray image may be improved.

Also, according to an embodiment, a final x-ray image having the best image quality may be generated by removing scattering by repeatedly performing a material decomposition operation and a scatter estimation operation. Accordingly, second information and third information may be obtained based on the final X-ray image, and the accuracy of the second information and the third information may be improved.

While the disclosure has been particularly shown and described with reference to embodiments thereof, they are provided for the purposes of illustration and it will be understood by one of ordinary skill in the art that various modifications and equivalent other embodiments may be made without departing from the scope defined by the claims.

What is claimed is:
1. An X-ray image processing method comprising:
obtaining a first X-ray image of an object including a plurality of materials comprising a first material and a second material different from the first material;

obtaining three-dimensional (3D) information about the object using a 3D camera;
obtaining first information about a thickness of the object based on the 3D information;
decomposing the first material from the object using the first information and the first X-ray image corresponding to a single energy band; and
obtaining second information related to a stereoscopic structure of the first material based on the decomposed first material.

2. The X-ray image processing method of claim 1, further comprising obtaining third information related to a stereoscopic structure of the second material, based on the first information and the second information.

3. The X-ray image processing method of claim 1, wherein the second information is obtained based on the first information and X-ray absorption characteristics shown in the first X-ray image.

4. The X-ray image processing method of claim 2, wherein the first material is soft tissue, and
wherein the second material is a bone.

5. The X-ray image processing method of claim 4, wherein the second information comprises at least one of a thickness of the soft tissue, a volume of the soft tissue, a volume ratio of the soft tissue, and an areal density of the soft tissue, and
the third information comprises at least one of a thickness of the bone, a volume of the bone, a volume ratio of the bone, and an areal density of the bone.

6. The X-ray image processing method of claim 2, wherein the second information comprises information about a thickness of the first material, and
wherein the third information comprises information about a thickness of the second material.

7. An X-ray image processing method comprising:
obtaining a first X-ray image of an object including a plurality of materials comprising a first material and a second material different from the first material;
obtaining three-dimensional (3D) information about the object using a 3D camera;
obtaining first information about a thickness of the object based on the 3D information; and
obtaining second information related to a stereoscopic structure of the first material by decomposing the first material from the object using the first information and the first X-ray image;
obtaining third information related to a stereoscopic structure of the second material, based on the first information and the second information; and
performing scatter correction on the first X-ray image, based on the second information and the third information.

8. The X-ray image processing method of claim 1, further comprising measuring a distance from the 3D camera to a surface of the object, based on the 3D information,
wherein the first information about the thickness of the object is obtained based on the distance to the surface of the object.

9. An X-ray image processing method comprising:
obtaining a first X-ray image of an object including a plurality of materials comprising a first material and a second material different from the first material;
obtaining three-dimensional (3D) information about the object using a 3D camera;
obtaining first information about a thickness of the object based on the 3D information; and obtaining second information related to a stereoscopic structure of the first material by decomposing the first material from the object using the first information and the first X-ray image;
obtaining third information related to a stereoscopic structure of the second material, based on the first information and the second information;
obtaining a scatter-corrected first X-ray image, by performing scatter correction on the first X-ray image based on the second information and the third information; and
updating the second information and the third information based on the scatter-corrected first X-ray image.

10. The X-ray image processing method of claim 9, further comprising generating, based on the second information and the third information, a scatter map showing a distribution of a scattered X-ray in the first X-ray image; and
wherein the scatter-corrected first X-ray image is obtained by using the scatter map to remove a noise signal corresponding to the scattered X-ray from the first X-ray image.

11. The X-ray image processing method of claim 10, further comprising:
obtaining, based on the second information and the third information, a first virtual X-ray image by performing projection simulation on the object; and
determining whether to update the second information, the third information, and the scatter map based on a result of a comparison between the first virtual X-ray image and the first X-ray image.

12. The X-ray image processing method of claim 11, further comprising:
generating, through the projection simulation, a projection image by transmitting an incident X-ray through a phantom corresponding to the object; and
generating, based on the second information and the third information, the scatter map showing the distribution of the scattered X-ray in the first X-ray image,
wherein the first virtual X-ray image is obtained by adding the projection image and the scatter map.

13. The X-ray image processing method of claim 2, further comprising outputting a user interface screen comprising at least one of the first information, the second information, or the third information.

14. The X-ray image processing method of claim 1, wherein the first X-ray image is obtained by emitting an X-ray having a single energy band to the object.

15. An X-ray image processing apparatus comprising:
a data interface configured to:
obtain a first X-ray image of an object including a plurality of materials comprising a first material and a second material different from the first material; and
obtain three-dimensional (3D) information about the object using a 3D camera; and
an image processor comprising at least one processor configured to execute at least one instruction to:
obtain first information about a thickness of the object based on the 3D information,
decompose the first material from the object using the first information and the first X-ray image corresponding to a single energy band, and
obtain second information related to a stereoscopic structure of the first material based on the decomposed first material.

16. The X-ray image processing apparatus of claim 15, wherein the image processor is further configured to execute the at least one instruction to obtain third information related to a stereoscopic structure of the second material based on the first information and the second information.

17. The X-ray image processing apparatus of claim 15, wherein the first material is soft tissue, and
wherein the second material is a bone.

18. An X-ray image processing apparatus comprising:
a data interface configured to:
obtain a first X-ray image of an object including a plurality of materials comprising a first material and a second material different from the first material; and
obtain three-dimensional (3D) information about the object using a 3D camera; and
an image processor comprising at least one processor configured to execute at least one instruction to:
obtain first information about a thickness of the object based on the 3D information,
obtain second information related to a stereoscopic structure of the first material by decomposing the first material from the object using the first information and the first X-ray image,
obtain third information related to a stereoscopic structure of the second material based on the first information and the second information, and
perform scatter correction on the first X-ray image based on the second information and the third information.

19. The X-ray image processing apparatus of claim 15, wherein the image processor is further configured to execute the at least one instruction to measure a distance from the 3D camera to a surface of the object based on the 3D information and to obtain the first information about the thickness of the object based on the distance to the surface of the object.

20. A non-transitory computer-readable medium storing instructions which, when executed by at least one processor, cause the at least one processor to execute an X-ray image processing method on a computer, the X-ray image processing method comprising:
obtaining a first X-ray image of an object including a plurality of materials comprising a first material and a second material different from the first material;
obtaining three-dimensional (3D) information about the object by using a 3D camera;
obtaining first information about a thickness of the object based on the 3D information; and
decomposing the first material from the object using the first information and the first X-ray image to obtain second information related to a stereoscopic structure of the first material.

21. The method of claim 1, further comprising performing scatter correction on the first X-ray image based on the first information and the second information.

* * * * *